United States Patent [19]

Sakamoto et al.

[11] Patent Number: 5,096,292

[45] Date of Patent: Mar. 17, 1992

[54] BORESCOPE APPARATUS

[75] Inventors: Nobuyuki Sakamoto; Ichiro Takahashi; Morihide Mizumoto, all of Hachioji; Saburo Hosono, Hino; Tutomu Yamamoto, Hachioji; Minoru Okada, Sagamihara; Shinichi Nishigaki, Tokyo; Yoshio Shishido, Sagamihara; Kazuhiro Misono; Atsushi Miyazaki, both of Hachioji; Yasuhiro Ueda, Kokubunji; Toshiaki Nishikori, Sagamihara; Takeaki Nakamura, Hino; Eiichi Fuse, Hachioji; Akibumi Ishikawa, Hachioji; Yoshisada Aoki, Hachioji, all of Japan

[73] Assignee: Olympus Optical Co., Ltd., Tokyo, Japan

[21] Appl. No.: 442,320

[22] Filed: Nov. 28, 1989

Related U.S. Application Data

[63] Continuation-in-part of Ser. No. 241,078, Sep. 6, 1988, Pat. No. 4,991,957.

[30] Foreign Application Priority Data

| Apr. 25, 1989 | [JP] | Japan | 1-48556[U] |
| Apr. 25, 1989 | [JP] | Japan | 1-105290 |
| Apr. 28, 1989 | [JP] | Japan | 1-110408 |
| Apr. 28, 1989 | [JP] | Japan | 1-110409 |
| Aug. 2, 1989 | [JP] | Japan | 1-200764 |

[51] Int. Cl.[5] .................................... G02B 23/26
[52] U.S. Cl. ............................... 356/241; 128/6
[58] Field of Search ............. 356/241; 128/4, 6; 358/213.23; 385/117; 350/96.26

[56] References Cited

U.S. PATENT DOCUMENTS

| 4,189,944 | 2/1980 | Day et al. | 73/623 |
| 4,382,267 | 5/1983 | Angle | 358/213.23 |
| 4,485,668 | 12/1984 | Hudson et al. | 73/40.5 A |
| 4,575,185 | 3/1986 | Wentzell et al. | 350/96.26 |
| 4,653,478 | 3/1987 | Nagasaki et al. | 128/6 |
| 4,686,963 | 8/1987 | Cohen et al. | 350/96.26 |
| 4,735,501 | 4/1988 | Ginsburgh et al. | 356/241 |
| 4,784,117 | 11/1988 | Miyazaki | 128/4 |
| 4,784,463 | 11/1988 | Miyazaki | 128/4 |
| 4,793,326 | 12/1988 | Shishido | 356/241 |
| 4,883,355 | 11/1989 | Saghatchi et al. | 356/241 |

FOREIGN PATENT DOCUMENTS

| 0242428A2 | 10/1987 | European Pat. Off. |
| 3111497A1 | 10/1982 | Fed. Rep. of Germany |
| 3500544C1 | 9/1986 | Fed. Rep. of Germany |
| 3532885A1 | 3/1987 | Fed. Rep. of Germany |
| 1278965 | 1/1961 | France |
| 189604 | 11/1983 | Japan |
| 76714 | 5/1985 | Japan | 350/96.26 |
| 60-177262 | 9/1985 | Japan |
| 126526 | 6/1986 | Japan | 350/96.26 |
| 62-251639 | 11/1987 | Japan |
| 260115 | 11/1987 | Japan | 350/96.26 |
| 63-314980 | 12/1988 | Japan |

OTHER PUBLICATIONS

Stengel, R. F., "Mirror, Rod Optics Inspect Deep Bores", *Design News*, 20 Nov. 1978, pp. 62, 63.

*Primary Examiner*—Richard A. Rosenberger
*Attorney, Agent, or Firm*—Frishauf, Holtz, Goodman & Woodward

[57] ABSTRACT

A borescope apparatus comprising a flexible insertion section, a jet port formed at the insertion section, a moving device for supplying a compressed fluid to the jet port, whereby the insertion section is moved by an impellent force of the fluid ejected from the jet port, and a stabilizing device for steadily maintaining the position of the insertion section.

14 Claims, 22 Drawing Sheets

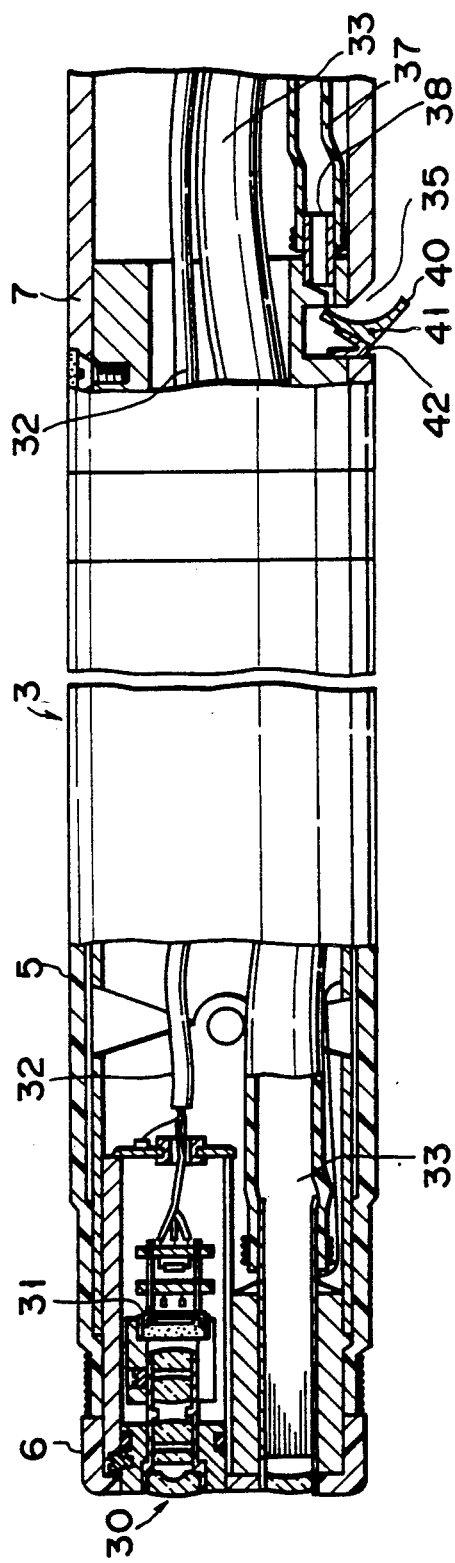
FIG. 2
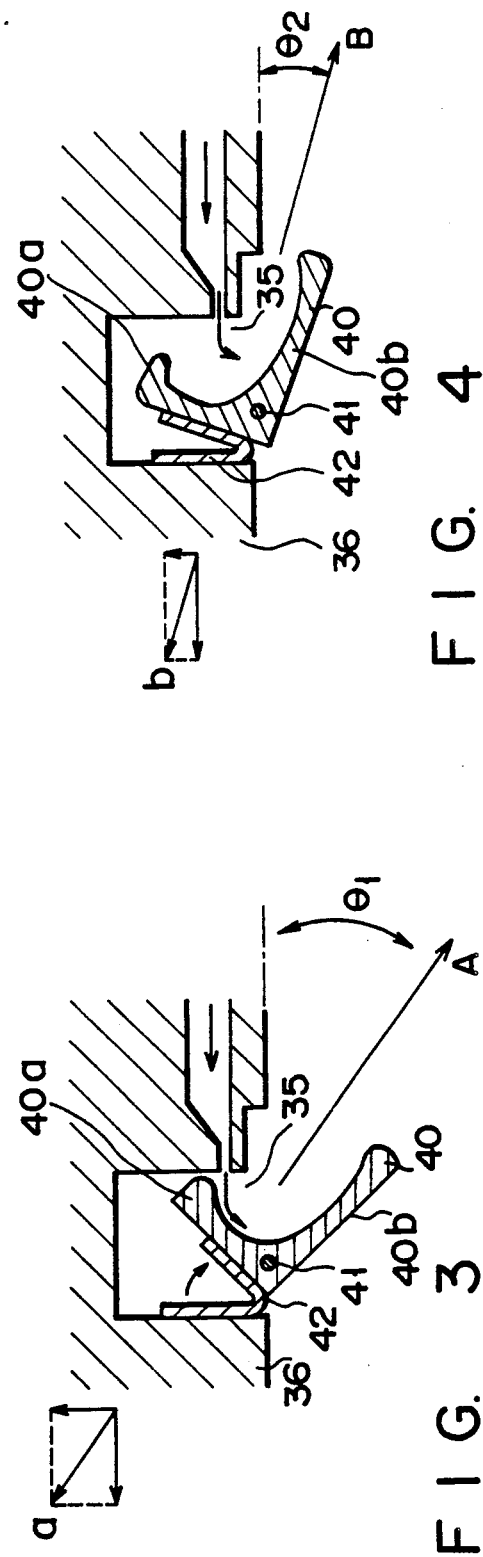
FIG. 4
FIG. 3

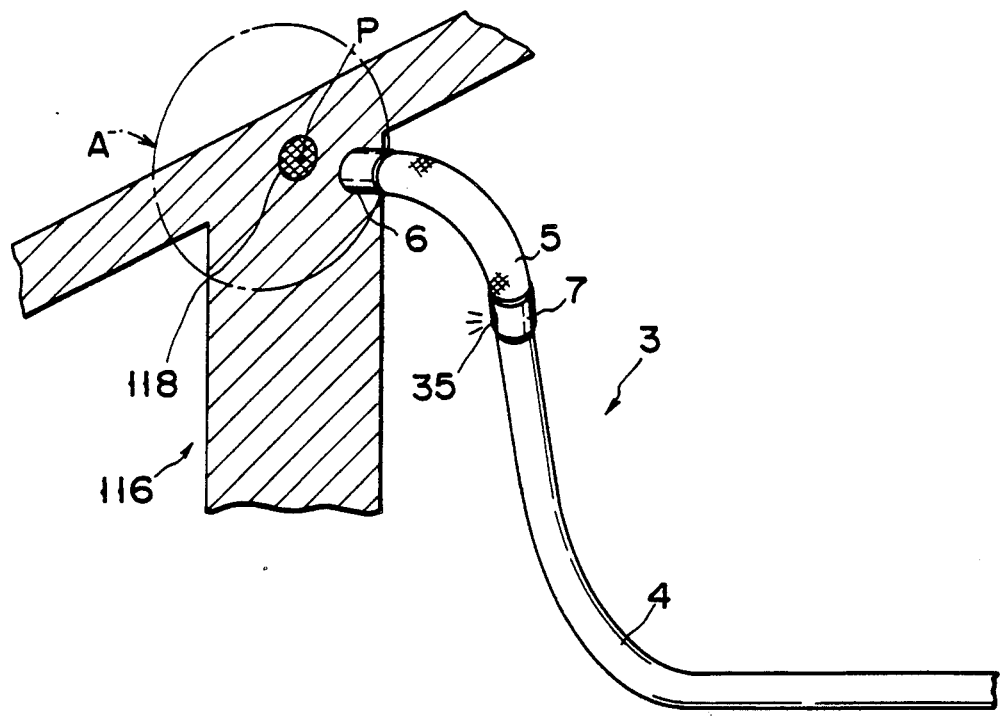
FIG. 11
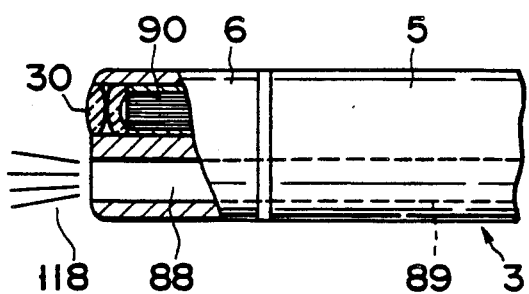 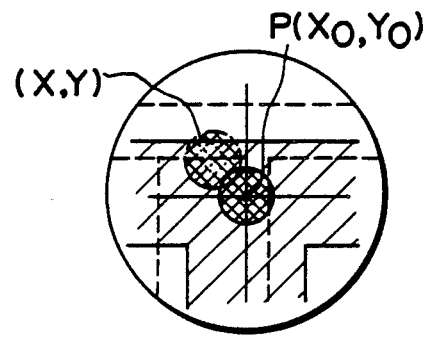
FIG. 12  FIG. 13

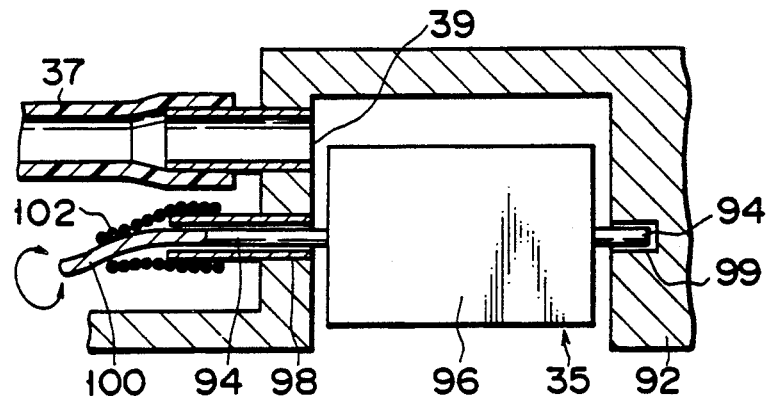
F I G. 14
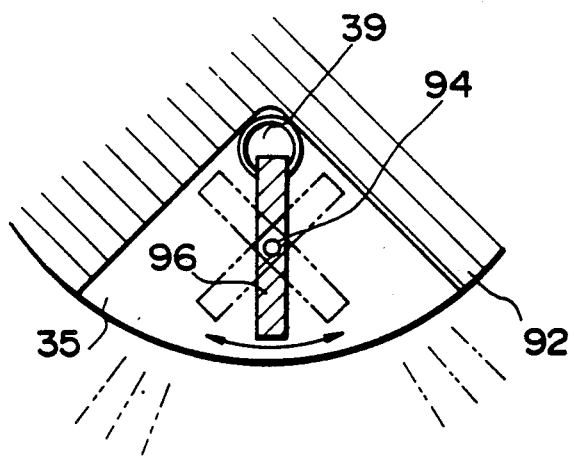
F I G. 15

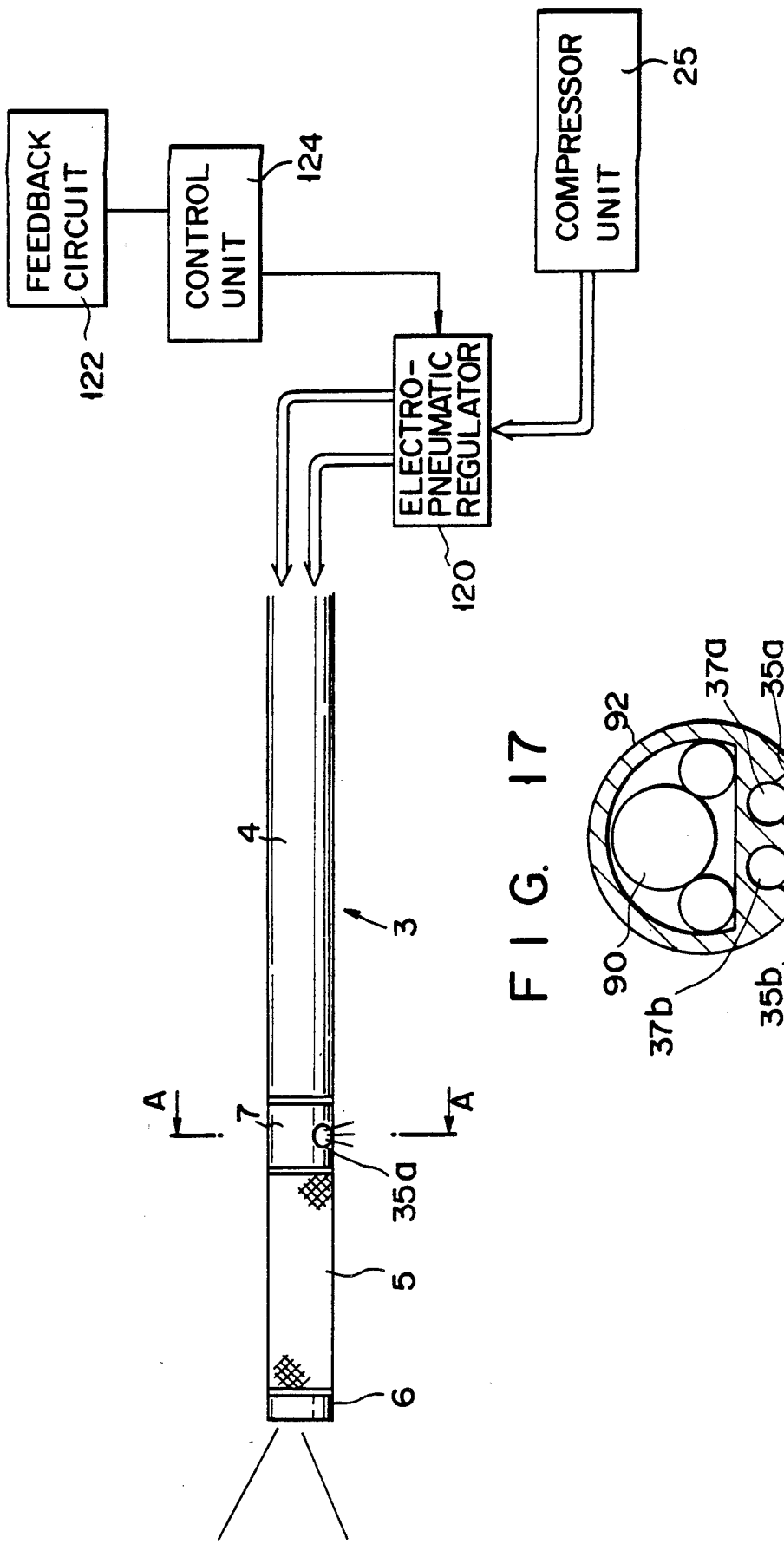

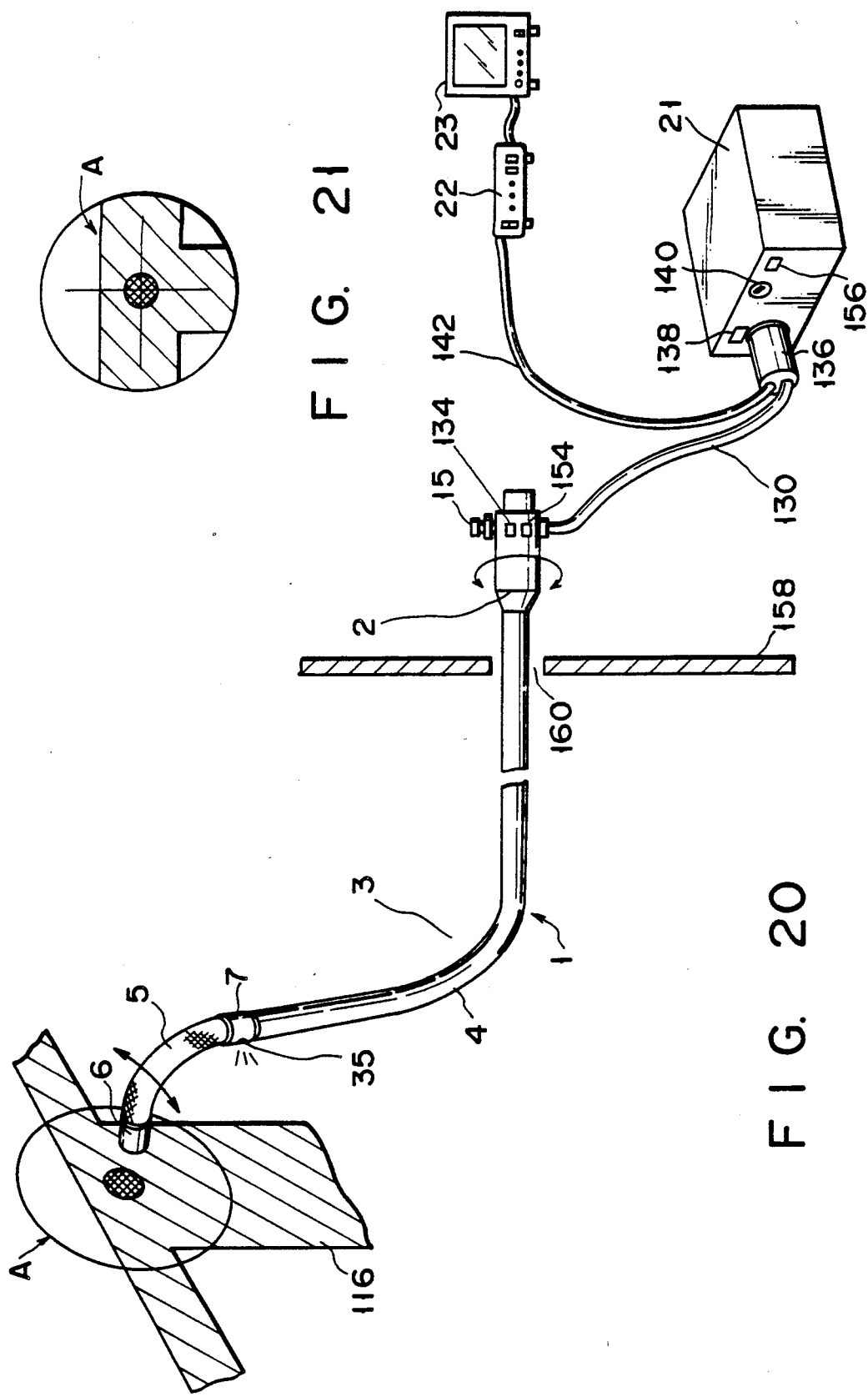

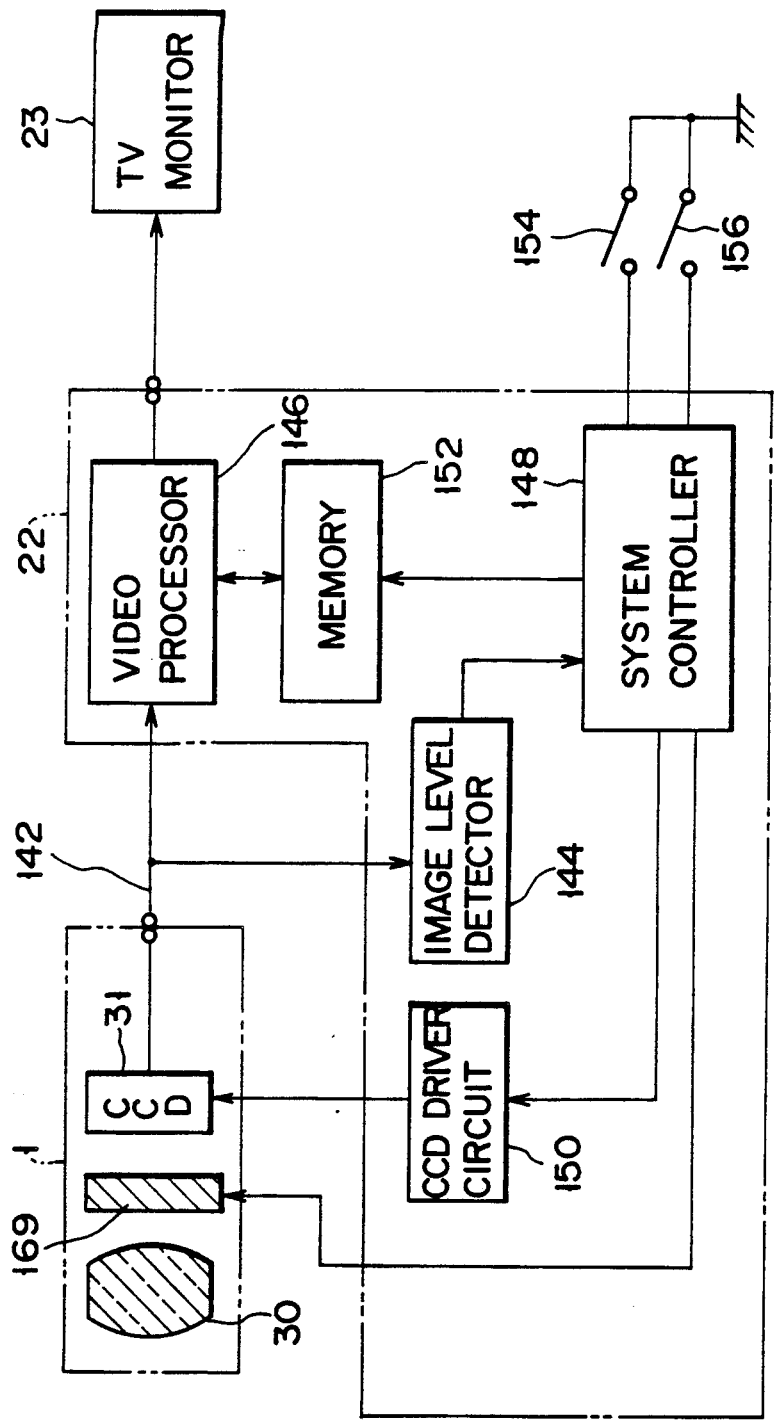
F I G. 23

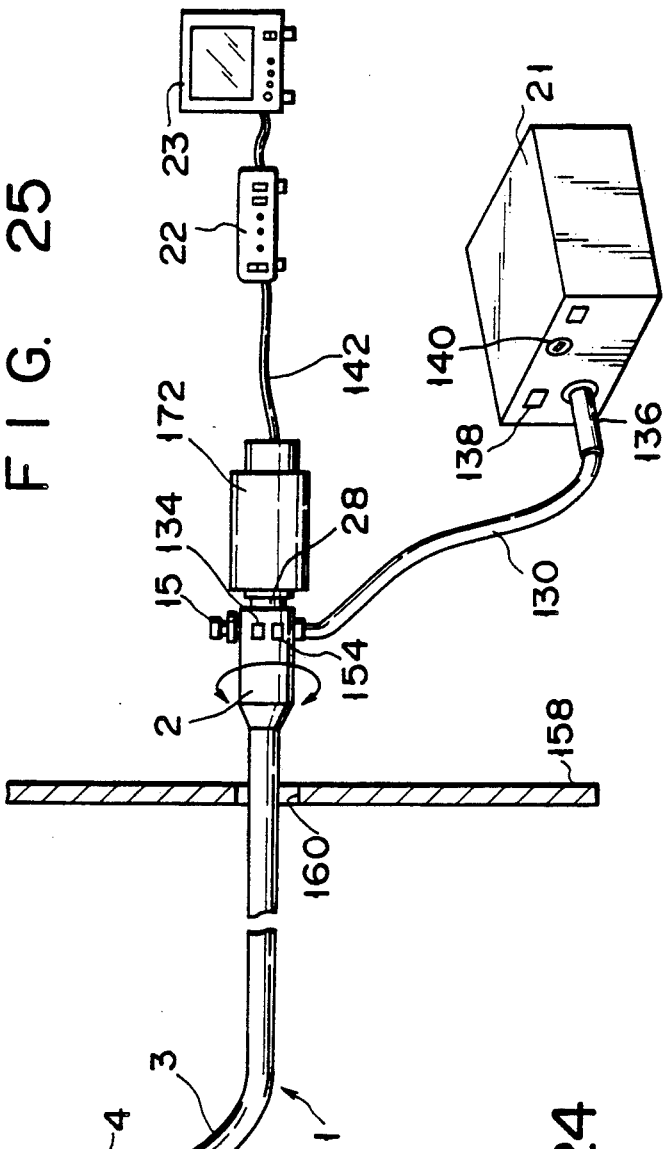
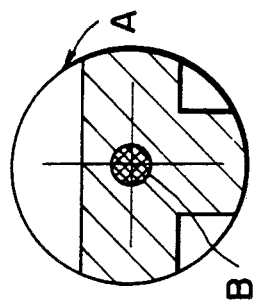
FIG. 25
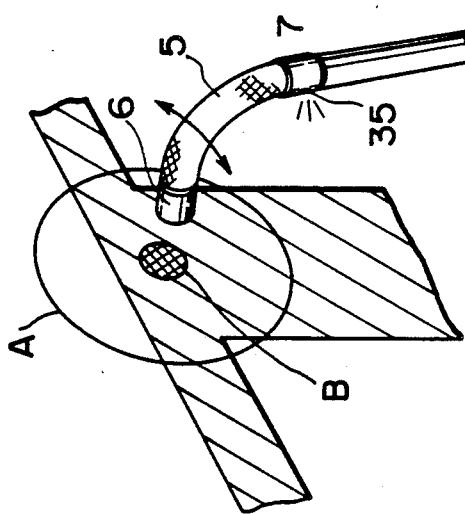
FIG. 24

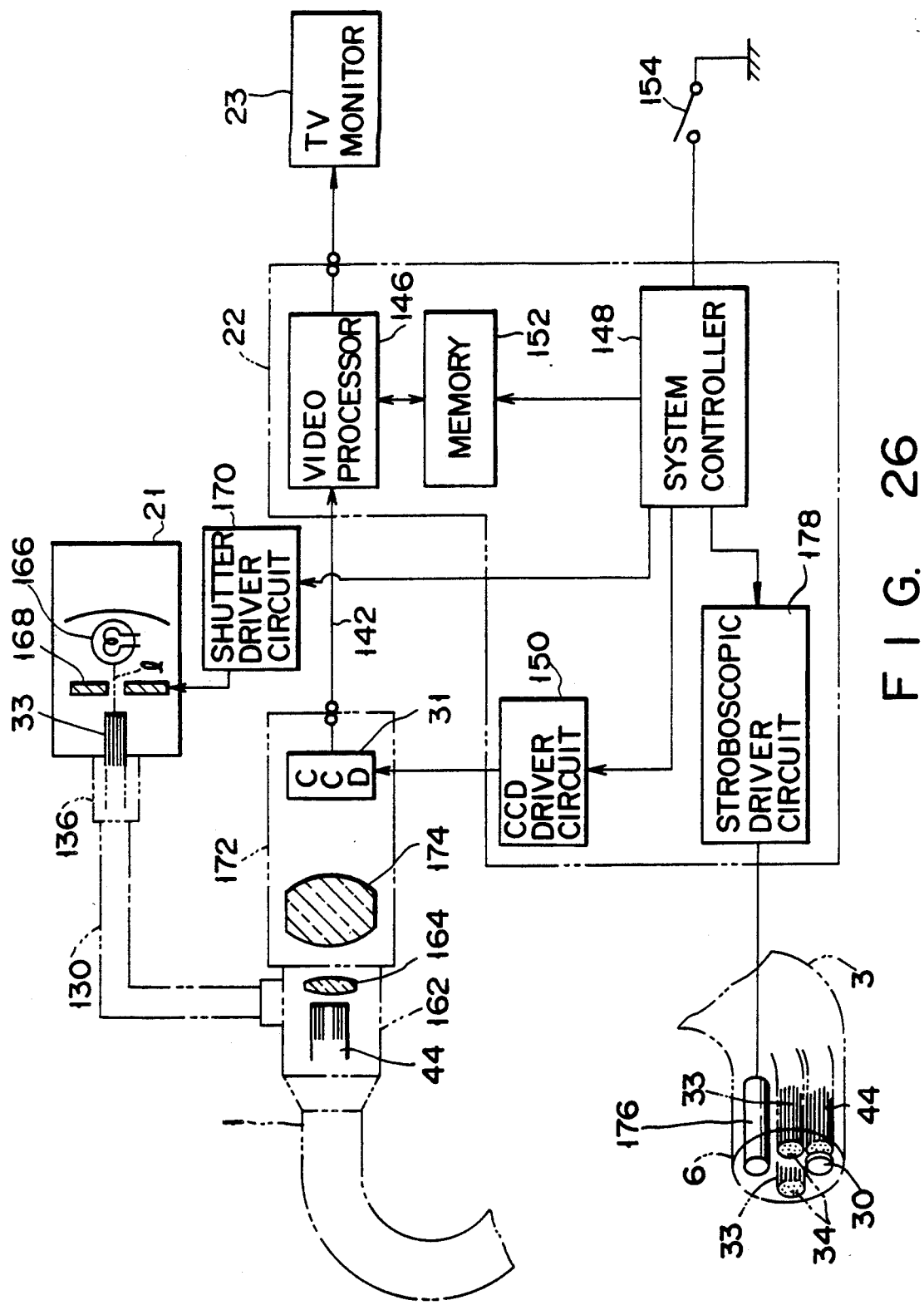
F I G. 26

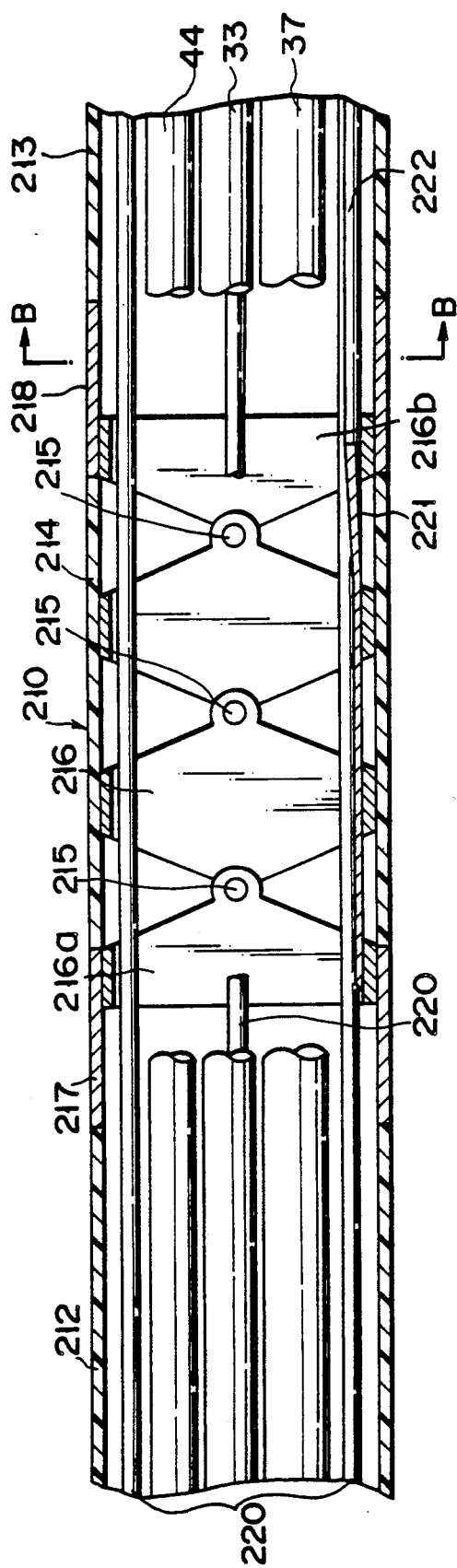
F I G. 32
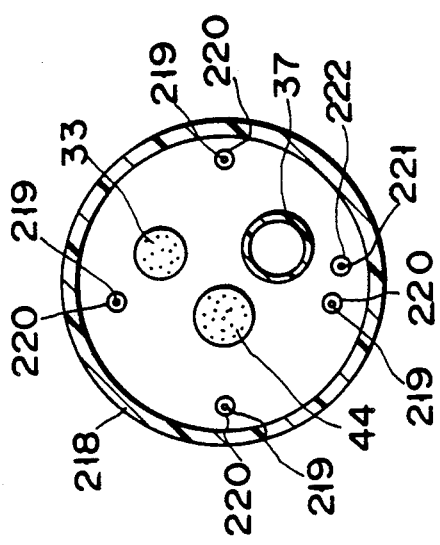
F I G. 33

BORESCOPE APPARATUS

CROSS-REFERENCES TO THE RELATED APPLICATIONS

The present application is a continuation-in-part application of U.S. patent application Ser. No. 241,078 filed on Sept. 6, 1988 now U.S. Pat. No. 4,991,957.

BACKGROUND OF THE INVENTION

1. Field of the Invention

The present invention relates to a borescope apparatus capable of jetting a compressed fluid from a jet port in an insertion section so that the insertion section is moved by the impellent force of the fluid jet.

2. Description of the Related Art

A typical industrial borescope apparatus is disclosed in U.S. Pat. No. 4,753,501, for example. In this borescope, a jet port is formed sidelong at the distal end portion of a flexible insertion section. A compressed fluid, such as high-pressure air, is jetted from the jet port so that the insertion section is subjected to reaction from the impellent force of the fluid jet. Thus, the insertion section can be moved opposite to the jet direction of the compressed fluid.

Many of the borescopes of this type are widely used for industrial applications. For example, they are used for the inspection of the interior of gas pipes, tanks, or wing cavities of large-sized airplanes. Since the insertion section of these borescopes can be raised, all the corners of even a vertically extending cavity can be observed through the insertion section.

According to these conventional borescopes, however, the insertion section is raised with the force of gravity and a thrust from a fluid jet delicately balanced, as its distal end portion is brought close to an objective region of inspection to facilitate the observation. In general, therefore, the raised posture of the insertion section is unstable. Consequently, the distal end of the insertion section is liable to a fine deflection during the observation, so that a stable image cannot be observed for a close inspection.

SUMMARY OF THE INVENTION

An object of the present invention is to provide a borescope apparatus which is improved so that a deflection of an insertion section raised by a thrust from a fluid jet can be restrained to ensure a stable observation image.

Another object of the invention is to provide a borescope apparatus which is improved so that a blur-free distinct still picture can be obtained even while the insertion section is being raised by the thrust from the fluid jet.

The above objects of the invention are achieved by a borescope apparatus constructed as follows. The borescope apparatus comprises: a flexible insertion section; a jet port formed at the insertion section; moving means for supplying a compressed fluid to the jet port, whereby the insertion section is moved by an impellent force of the fluid ejected from the jet port; and stabilizing means for steadily maintaining the position of the insertion section.

Preferably, the borescope apparatus according to the present invention comprises a borescope including a flexible insertion section, a jet port formed at the insertion section, and raising means for supplying a compressed fluid to the jet port, whereby the insertion section is raised by an impellent force of the fluid ejected from the jet port; a solid-state image sensing device attached to the borescope; time limiting means for limiting a charge storage time within the charge storage time of the solid-state image sensing device; signal processing means for converting a signal from the solid-state image sensing device into a video signal; and image processing means including memory means for storing the video signal and adapted to convert the video signal stored in the memory means into a freeze image.

Preferably, moreover, the borescope apparatus according to the present invention comprises the borescope; image sensing means including a solid-state image sensing device attached to the borescope, whereby an image of a field of view is picked up by the solid-state image sensing device; received light control means for controlling optical information received by the solid-state image sensing device; and image processing means including memory means for storing a video signal picked up by the solid-state image sensing device and adapted to convert the video signal stored in the memory means into a freeze image.

BRIEF DESCRIPTION OF THE DRAWINGS

FIG. 2 is a partial sectional view of an insertion section of the borescope apparatus shown in FIG. 1;

FIGS. 3 and 4 are longitudinal sectional views of a jet-angle control valve of the borescope apparatus;

FIG. 11 is a perspective view showing an operating state of a borescope apparatus according to a second embodiment of the present invention;

FIG. 12 is a partial sectional view of the distal end portion of an insertion section of the borescope apparatus shown in FIG. 11;

FIG. 13 is a diagrammatic view showing the field of view of the borescope apparatus of FIG. 11;

FIG. 14 is a longitudinal sectional view of injection-direction control means of the borescope apparatus;

FIG. 15 is a cross-sectional view of the injection-direction control means shown in FIG. 14;

FIG. 17 is a diagrammatic view showing a first modification of the borescope apparatus of FIG. 11;

FIG. 18 is a sectional view taken along line A—A of FIG. 17;

FIG. 20 is a perspective view showing an operating state of a borescope apparatus according to a third embodiment of the present invention;

FIG. 21 is a diagrammatic view showing the field of view of the borescope apparatus shown in FIG. 20;

FIG. 23 is a block diagram showing a modification of the borescope apparatus according to the third embodiment;

FIG. 24 is a perspective view showing an operating state of a borescope apparatus according to a fourth embodiment of the present invention;

FIG. 25 is a diagrammatic view showing the field of view of the borescope apparatus shown in FIG. 24;

FIG. 26 is a block diagram showing a control circuit of the borescope apparatus of FIG. 24;

FIG. 32 is a longitudinal sectional view of an insertion section of the borescope apparatus shown in FIG. 31; and FIG. 33 is a sectional view taken along line B—B of FIG. 32.

DETAILED DESCRIPTION OF THE PREFERRED EMBODIMENTS

Preferred embodiments of the present invention will now be described with reference to the accompanying drawings.

Figure 1:
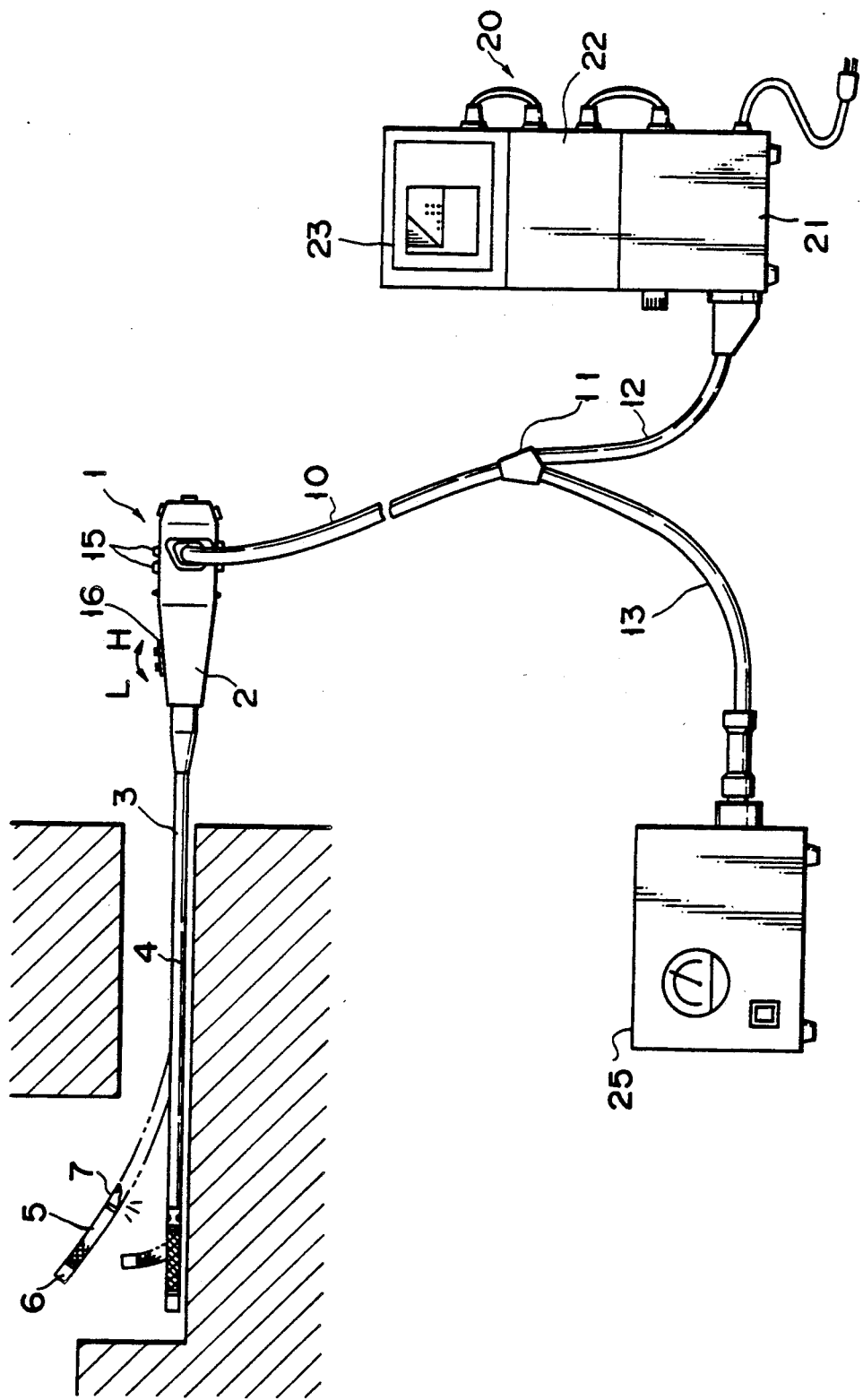
FIG. 1 is a side view of a borescope apparatus according to a first embodiment of the present invention.

FIGS. 1 to 4 show a first embodiment of the present invention. FIG. 1 is a side view showing an outline of a system including a borescope apparatus according to the first embodiment. The borescope system comprises electronic borescope 1, image processing system 20, and compressor unit 25.

Electronic borescope 1 comprises operating section 2 at its proximal end portion and elongate insertion section 3 connected to section 2. Insertion section 3 includes flexible tube portion 4 extending from operating section 2, bending tube portion 5 connected to the distal end of portion 4, and distal end piece 6 connected to the distal end of portion 5.

Operating section 2 is fitted with one end of cable 10, which connects electronic borescope 1 with image processing system 20 and compressor unit 25. Cable 10 has diverging portion 11 in the middle. One branch cable or light-source-side cable 12, diverging from portion 11, is connected to image processing system 20, while the other branch cable or compressor cable 13 is connected to compressor unit 25.

Image processing system 20 comprises light source unit 21 and camera control unit (CCU) 22. TV monitor 23 is connected to CCU 22.

Insertion section 3 of electronic borescope 1 is constructed in the manner shown in FIG. 2.

Objective optical system 30 is attached to the distal end face of distal end piece 6 at the distal end portion of bending tube portion 5, solid-state image sensing device o charge-coupled device (CCD) 31 is provided at the rear end portion of system 30. CCD 31 is connected to image processing system 20 by means of electric cable 32. Thus, an optical image incident on objective optical system 30 is converted into an electrical signal by CCD 31, and the signal is transmitted through cable 32 to system 20.

The distal end portion of light guide 33, which extends parallel to objective optical system 30, is attached to the distal end face of distal end piece 6. The other end of guide 33 is connected to light source unit 21 by means of cable 10 and light-source-side cable 12.

Jet port structure 7 having one or more high-pressure air jet ports 35 is attached to that part of insertion section 3 between flexible tube portion 4 and bending tube portion 5.

Each jet port 35 opens at right angles to the axial direction of insertion section 3, and is connected to air tube 37 passed through section 3. One end of tube 37 is connected to jet port 35 by means of connecting pipe 38, while the other end of tube 37 is connected to compressor unit 25 by means of compressor cable 13.

Connecting pipe 38 extends substantially at right angles to jet port 35.

Jet port 35 is provided with jet-angle control valve 40 according to the first embodiment of the present invention. Valve 40 is substantially L-shaped, and its bent central portion is rockably supported on jet port structure 7 by means of pivot pin 41.

One wall 40a of jet-angle control valve 40 is opposed to connecting pipe 38, and receives high-pressure air ejected from pipe 38. Leaf spring 42, which is disposed between wall 40a and structure 7, continually urges valve 40 to rock in the clockwise direction of FIGS. 2 to 4.

Thus, if the high-pressure air is not supplied from compressor unit 25, jet-angle control valve 40 is rocked by the urging force of leaf spring 42, as shown in FIG. 3. If the high-pressure air, compressed to a predetermined pressure or more, is supplied from unit 25, on the other hand, valve 40 is pressed by the air pressure, and rocks against the urging force of spring 42, as shown in FIG. 4.

Angle knobs 15 an pressure control switch 16 are arranged on operating section 2 of borescope 1. Knobs 15 are used to operate angle wires (not shown) to bend bending tube portion 5. Switch 16 is used to control the output of compressor unit 25 to adjust the pressure of the high-pressure air ejected from each jet port 35.

The following is a description of the operation of the borescope apparatus according to the first embodiment with the aforementioned construction.

In inserting the borescope into a cave which has a narrow inlet passage and a stepped passage portion, as shown in FIG. 1, the stepped portion cannot be got over by only operating angle knobs 15 of operating section 2 to bend bending tube portion 5, as indicated by an imaginary line in FIG. 1. In such a case, the high-pressure air is ejected from jet port 35 to raise insertion section 3.

In raising insertion section 3, pressure control switch 16 is operated to supply the high-pressure air from compressor unit 25 to jet port 35 through compressor cable 13, air tubes 37, and connecting pipes 38. Thereupon, insertion section 3 is subjected to an impellent force in the direction opposite to the opening direction of jet port 35, by the high-pressure air jet, thereby bending or rising.

In the first embodiment, each jet port 35 is provided with jet-angle control valve 40, and is continually urged by leaf spring 42 to rock in the clockwise direction of FIGS. 2 to 4. If the high-pressure air is not supplied from compressor unit 25, therefore, valve 40 is rocked by the urging force of spring 42, as shown in FIG. 3.

If the pressure of the high-pressure air supplied from compressor unit 25 in this state is not high enough, the high-pressure air ejected from connecting pipe 38 runs against one wall 40a, and is jetted in the direction of arrow A along the other wall 40b. Since jet-angle control valve 40 is rocked in the clockwise direction by leaf spring 42, jet angle $\theta 1$ in the direction of arrow A is relatively wide. Thus, insertion section 3 is subjected to an impellent force in the direction of arrow a as a jet reaction force. Since this impellent force has a relatively great vector component upwardly directed at right angles to the axial direction of insertion section 3, it effectively serves to raise the insertion section.

Thus, a relatively great impellent force is needed to raise insertion section 3. Since jet angle $\theta 1$ is relatively wide, as mentioned before, the desired impellent force can be obtained.

While insertion section 3 is being raised in this manner, the pressure of the air supplied from compressor unit 25 attains the predetermined value or a higher level, and the high-pressure air from connecting pipe 38 runs against one wall 40a. Accordingly, jet-angle control valve 40 is rocked in the counterclockwise direction against the force of leaf spring 42, as shown in FIG. 4.

In this state, the high-pressure air is ejected in the direction of arrow B along the other wall 40b, and jet angle $\theta 2$ for this case is narrower than jet angle $\theta 1$ for the case of FIG. 3. Thus, insertion section 3 is subjected to an impellent force in the direction of arrow b as a jet reaction force. Since this impellent force has a relatively small vector component upwardly directed at right angles to the axial direction of insertion section 3, the force to raise the insertion section is small.

Once insertion section 3 is raised, it must only be kept raised horizontally, for example, without requiring any substantial impellent force no more. Thus, a stable raised state can be established by the impellent force for the rise.

When the supply of the high-pressure air from compressor unit 25 is stopped, the high-pressure air ceases to be ejected, and the impellent force dies away. Thus, insertion section 3 stops from rising.

In this case, jet-angle control valve 40 is restored by the force of leaf spring 42, as shown in FIG. 3. In raising insertion section 3 again, therefore, wide jet angle &H 1 can be obtained, so that section 3 can be raised quickly.

Thus, according to the first embodiment described above, a wide jet angle will have already been set by the time when the supply of the high-pressure air is started, so that insertion section 3 can be raised with speed.

Figure 5:
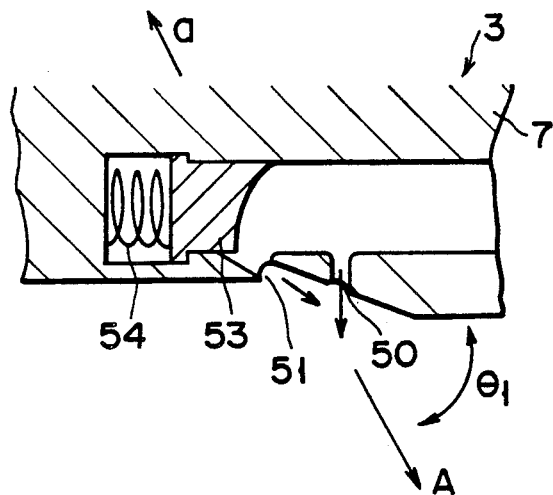
FIGS. 5 and 6 are longitudinal sectional views showing a first modification of the jet-angle control valve.
Figure 6:
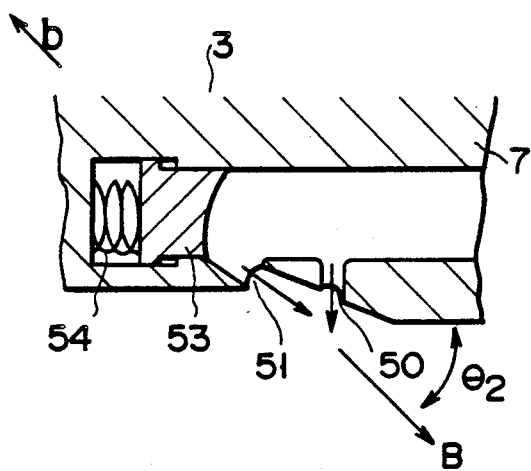

FIGS. 5 and 6 show a first modification of the jet-angle control valve.

In the first embodiment, jet-angle control valve 40 is of a rocking type. In this modification, the jet-angle control valve used is of a slide type.

As shown in FIG. 5, jet port structure 7 has main jet port 50 and auxiliary jet port 51 arranged in the axial direction of insertion section 3. Main jet port 50 opens at right angles to the axial direction of section 3, while auxiliary jet port 51 is inclined so that its extension intersects the extension of main port 50. Auxiliary port 51 is formed so that its opening degree can be varied by means of slide-type jet-angle control value 53, which is continually urged by the force of coil spring 54 to close auxiliary jet port 51. Valve 53, receiving the pressure of the high-pressure air supplied from compressor unit 25, is slid against the urging force of spring 54, thereby allowing auxiliary jet port 51 to open.

If the pressure of the air supplied from compressor unit 25 is not high enough, in the first modification constructed in this manner, jet-angle control valve 53 is urged by the force of coil spring 54 to reduce the opening area of auxiliary jet port 51, as shown in FIG. 5. Accordingly, the amount of air ejected from auxiliary jet port 51 is smaller than the amount of air ejected from main jet port 50, and jet angle $\theta 1$ of joint flow A of the airs from ports 51 and 51 is relatively wide.

As a result, the impellent force in the direction of arrow a is applied to insertion section 3, thus effectively serving to raise the insertion section.

While insertion section 3 is being raised, the pressure of the air supplied from compressor unit 25 usually attains the predetermined value or a higher level. As shown in FIG. 6, therefore, jet-angle control valve 53 is slid against the urging force of coil spring 54, thereby allowing auxiliary jet port 51 to open wide.

In this state, the amount of air ejected from auxiliary jet port 51 is relatively large, and jet angle $\theta 2$ of joint flow B of the airs from main and auxiliary jet ports 50 and 51 is narrower. Accordingly, the impellent force in the direction of arrow b is applied to insertion section 3. Since this direction is inclined at a substantial angle to the axial direction of section 3, the force to raise section 3 is small.

Once the section 3 is raised, therefore, the stable raised state can be maintained by the reduced impellent force.

Figure 7:
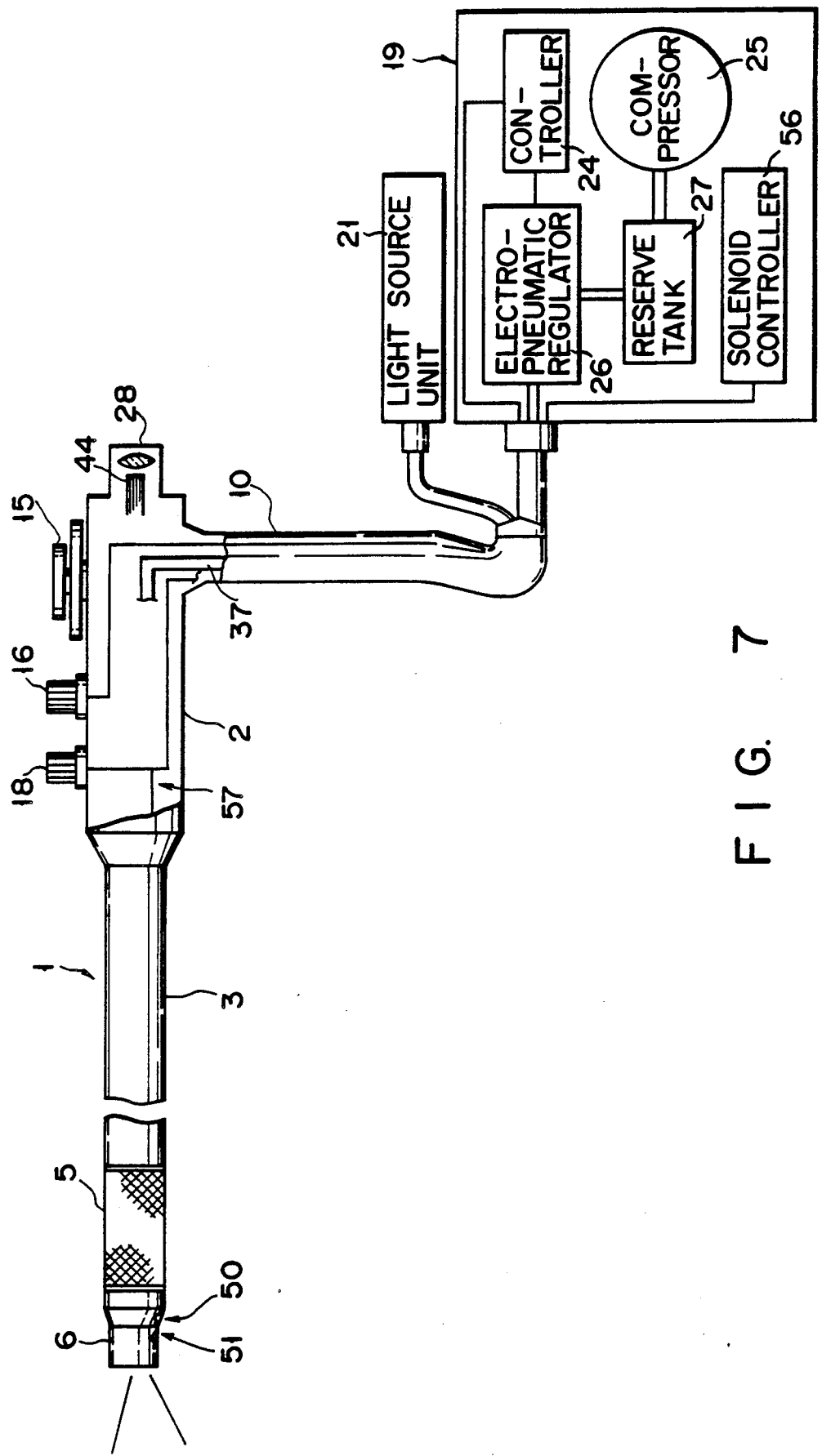
FIG. 7 is a diagrammatic view of a borescope apparatus with a jet-angle control valve according to a second modification.
Figure 8:
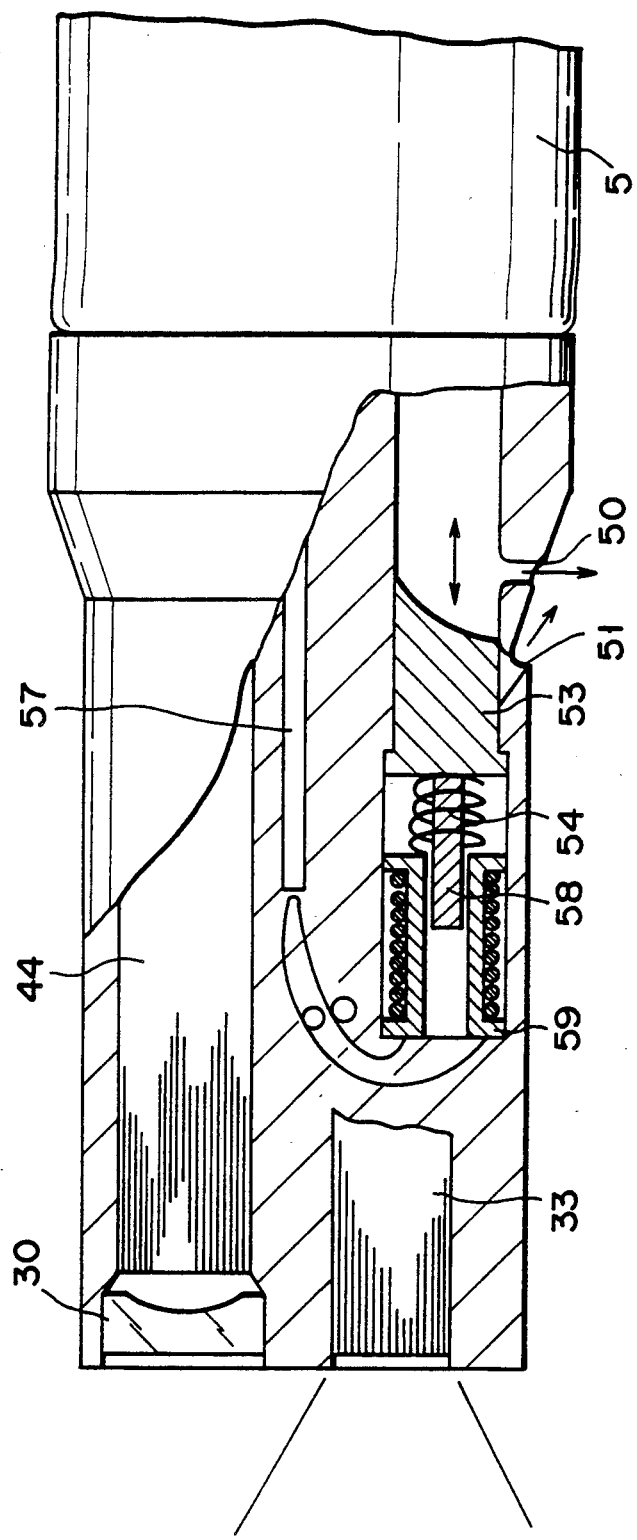
FIG. 8 is a partial sectional view of the distal end portion of an insertion section of the borescope apparatus shown in FIG. 7.

FIGS. 7 and 8 show a second modification. A borescope apparatus according to this modification comprises optical borescope 1 having image guide 44, control unit 19, and light source unit 21. Electropneumatic regulator 26 is connected to air tube 37 which communicates with main and auxiliary jet ports 50 and 51 at distal end piece 6 of insertion section 3. Regulator 26 is connected to compressor unit 25 through reserve tank 27. The compressed air supplied from unit 25 is controlled by electropneumatic regulator 26, which is adjusted by means of a control signal from controller 24 connected to pressure control switch 16.

As shown in FIG. 8, slide-type jet-angle control valve 53, which is provided inside the jet ports, is fitted with permanent magnet 58. Electromagnet or solenoid coil 59, which is connected to solenoid controller 56 by means of solenoid control cable 57, is located in front of valve 53. Magnet 58 is slidably inserted in coil 59. Coils spring 54 is disposed between coil 59 and valve 53. Jet-angle control switch 18 is connected to controller 56.

Thus, in this second modification, jet-angle control switch 18 is operated to drive solenoid controller 56, so that a control signal is transmitted through solenoid control cable 57 to solenoid coil 59. In accordance with this control signal, magnetic force produced in coil 59 is regulated, and the length of permanent 58, which is drawn into coil 59 against the urging force of coil spring 54, is adjusted. As a result, the position of jet-angle control valve 53 fixed to magnet 58 is adjusted. In this manner, the flow rate of the air jet from auxiliary jet port 51 can be controlled.

Figures 9, 10:
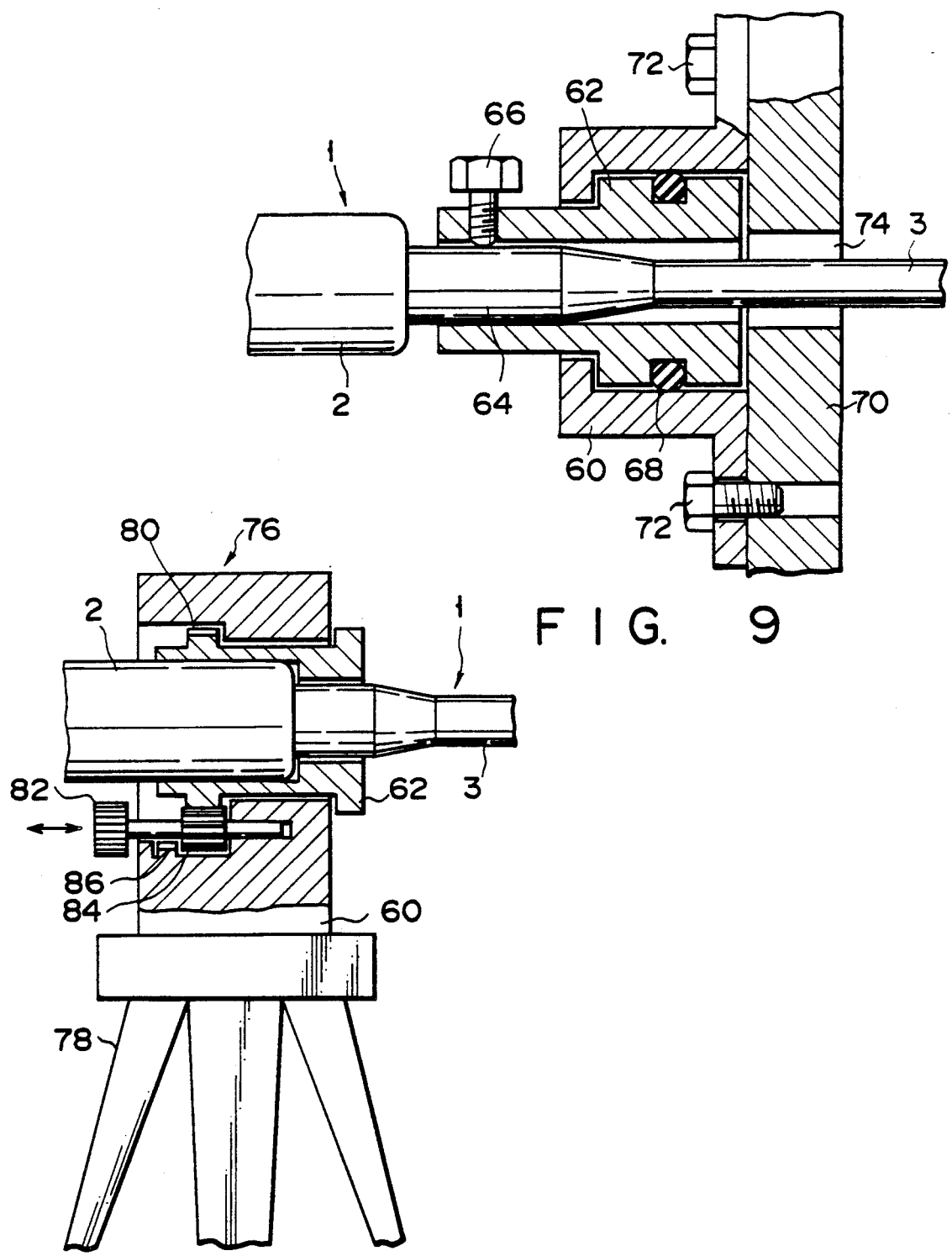
FIG. 9 is a sectional view of a principal part of a rotating unit for rotating the insertion section of the borescope apparatus.
FIG. 10 is a partial sectional view of the rotating unit.

Referring now to FIG. 9, a rotating unit for rotating the insertion section of the borescope apparatus will be described.

This rotating unit is provided with retaining means for rotatably retaining operating section 2 of borescope 1, whereby insertion section 3 of the borescope can be rotated easily and securely in the circumferential direction.

More specifically, the rotating unit comprises fixed jig 60 and movable jig 62. Movable jig 62 is rockably fitted in fixed jig 60, and is mounted on reinforcement portion 64 at the proximal end of insertion section 3 of borescope 1. Borescope 1 is fixed to jig 62 by means of fixing screw 66. In this arrangement, borescope 1 and movable jig 62 can rotate integrally with fixed jig 60.

O-ring 68 is fitted on a fitting portion of movable jig 62. It is pressed against the inner peripheral surface of a fitting portion of fixed jig 60, thereby producing a frictional force, so that borescope 1 can be fixed in any desired rotational position.

Fixed jig 60 is provided with jig fixing screws 72 which are used to secure jig 60 to outer wall 70 or the like of an object of observation. Wall 70 has hole 74 in which insertion section 3 of borescope 1 is inserted.

In borescope 1, as described in connection with the first embodiment, jet ports for jetting a fluid are arranged at the distal end portion of insertion section 3 so that the distal end portion can be raised by means of a thrust from the jetted fluid.

In the borescope rotating unit described above, fixed jig 60 is fixedly mounted on outer wall 70 or the like of the object of observation. Insertion section 3 of borescope 1 is inserted into the object through movable jig 62. Reinforcement portion 64 of insertion section 3 is secured to jig 62 so that borescope 1 is fixed. Thus, borescope 1 and movable jig 62 can rotate integrally with each other.

The interior of the object of observation can be observed by raising insertion section 3 of borescope 1. In doing this, operating section 2 of borescope 1 is slightly twisted to reorient the jet ports at the distal end portion of insertion section 3, thereby shifting the position of the raised distal end portion, in order to direct the field of observation to a target region to be observed.

Since insertion section 3 is raised in a delicate balance by the gas jet, troublesome, highly skilled operation is generally needed to quickly direct the distal end portion as required. In this embodiment, however, fixed jig 60 is rocked together with movable jig 62 fitted therein, so that the amount of rotation of insertion section 3 can be finely adjusted. Since movable jig 62 rotates relatively to fixed jig 60 while being subjected to the frictional force of O-ring 68, moreover, the direction of the distal end portion can be more finely adjusted, and movable jig 62 can be kept at any desired rotational position by the frictional force.

Thus, the direction of the jet ports can be steadily shifted little by little by the aforementioned operation. Accordingly, there is no possibility of the raised position being extremely changed, or the distal end portion of insertion section 3 abruptly turning sideways due to excessive twisting.

In this manner, the raised position of insertion section 3 being raised by the thrust of the fluid jet can be finely adjusted with ease, and quickly stabilized to ensure observation of a satisfactory image.

FIG. 10 shows a modification of the rotating unit. In this modification, the position of raised insertion section 3 can be finely adjusted by means of supporting device 76, which is adapted to retain operating section 2 of borescope 1. In supporting device 76, fixed jig 60 is mounted on the top face of tripod 78, and movable jig 62 for engagedly retaining operating section 2 is rockably fitted in jig 60. Movable jig 62 has external gear portion 80 thereon. Fixed jig 60 is provided with adjusting gear 84 with knob 82, corresponding to gear portion 80. Gear 84 is in mesh with gear portion 80 of movable jig 62.

Adjusting gear 84 is movable in the axial direction thereof, and can be detachably anchored to fixed tooth portion 86 on fixed jig 60. Gear 84, which normally is disengaged from tooth portion 86, as shown in FIG. 10, can be anchored to portion 86 by pulling and axially moving knob 82 of gear 84.

In raising and twisting insertion section 3 of borescope 1 supported by supporting device 76, knob 82 is turned to rotate movable jig 62 through the medium of adjusting gear 84 and gear portion 80. Thus, borescope 1, which is integrally connected to movable jig 62, can be accurately rotated. The direction and amount of this rotation can be freely selected. By this operation, the rotation of insertion section 3 can be finely adjusted, and the position of section 3 raised in a delicate balance can be set with accuracy.

Since the direction of the jet ports can be steadily shifted little by little by the aforementioned operation, there is no possibility of the raised position being extremely changed, or the distal end portion of insertion section 3 abruptly turning sideways due to excessive twisting.

In this manner, the raised position of insertion section 3 raised by the thrust of the fluid jet can be finely adjusted with ease, and quickly stabilized to ensure observation of a satisfactory image.

FIGS. 11 to 16 show a second embodiment of the borescope according to the present invention. As shown in FIG. 12, objective optical system 30 and channel port 88, along with a light guide and an illumination optical system, are provided at distal end portion 6 of borescope 1 according to the second embodiment. Optical system 30 is connected to an eyepiece optical system in an operating section by means of image guide 90 in insertion section 3. The illumination optical system and channel port 88 are connected to the light guide and channel 89, respectively, which are also arranged in insertion section 3.

Jet port structure 7, which is attached to that part of insertion section 3 between flexible tube portion 4 and bending tube portion 5, has jet port 35 for jetting a fluid. As shown in FIGS. 14 and 15, jet port 35 opens downwardly in the form of a fan. Air port 39 is formed at the central portion of fan-shaped jet port 35, and air tube 37 in insertion section 3 is connected to port 39. Tube 37 is also connected to compressor unit 25. The flow rate of the compressed fluid supplied from unit 25 to tube 37 can be suitably adjusted by means of a flow regulating portion.

Inside jet port 35, rockable jet-direction changing fin 96 is mounted on shaft 94. As shown in FIG. 14, the opposite end portions of shaft 94 are supported individually by means of bearings 98 and 99. Fin 96 is adapted to be selectively rocked from the neutral position indicated by full line in FIG. 15 to the positions indicated by broken lines on either side. As shown in FIG. 14, operating wire 100 is connected to shaft 94 of fin 96. Fin 96 is rocked by means of a rotatory force transmitted through wire 100.

Operating wire 100 is guided into the operating section through wire guide 102 which is formed of a closely wound coil, and is rotated by means of a drive motor (not shown). Also, wire 100 can be operated manually.

This arrangement constitutes jet-direction control means 104 for selecting the position of fin 96 in jet port 35 and redirecting the fluid ejected from port 35. Control means 104 constitutes operating means 106 which changes the position of raised insertion section 3 by redirecting the fluid jet from jet port 35.

Further, the borescope incorporates deflection detecting means for detecting the deflective displacement of the raised distal end portion of insertion section 3. The deflection detecting means may be of various types. The detecting means used in this embodiment is of a type such that the deflective displacement is detected by processing an image sensed through the borescope. More specifically, an image of field A observed through objective optical system 30 is sensed by means of image sensing means 108, such as a TV camera, and is observed through a TV monitor. The positions of reference points in sensed images in individual frames are compared by means of image processing apparatus 110, and movements (deviations) of the reference points are detected. Thus, image sensing means 108 and image processing apparatus 110 constitute detecting means 112 for detecting the displacement of insertion section 3 due to deflection.

Figure 16:
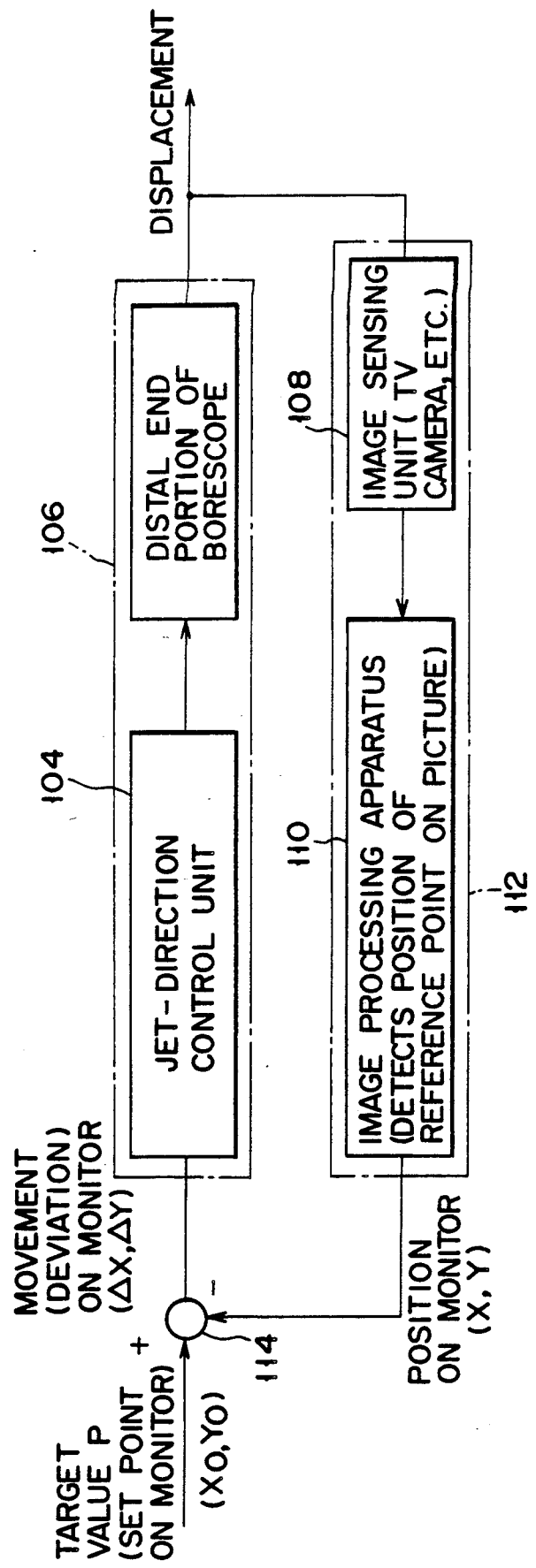
FIG. 16 is a block diagram showing a control circuit of the borescope apparatus of FIG. 11.

The control system shown in FIG. 16 constitutes feedback control means which feeds back a signal from deflection detecting means 112 to comparator 114, thereby adjusting the operation by jet-direction control means 104 so that the displacement of the raised distal end portion of insertion section 3 becomes zero.

The following is a more specific description of the operation of the borescope apparatus constructed in this manner. First, insertion section 3 of the borescope is introduced into interior 116 of an object of inspection, and compressed air is then supplied from an air source to jet port 35 through air tube 37. Thereupon, the air is jetted from port 35, so that the distal end portion of insertion section 3 rises, as shown in FIG. 11. If necessary, bending tube portion 5 is remotely bent to be directed to field A to be observed.

Colored marker material (e.g., paint) 118 is fed through channel 89 of insertion section 3, and is ejected through channel port 88 to be sprayed on part of the field to be observed. As a result, marker material 118 sticks to part of the field of view. The center of material 118 on the field is regarded as reference point P. Instead of setting the reference point by applying the marker material in this manner, reference point P may be defined, for example, as the center of the head of a rivet in interior 116 of the object of inspection, the rivet head being painted in advance. Alternatively, moreover, the configuration of the object may be utilized directly for this purpose.

As shown in FIG. 13, a set point on a screen is situated in the center (indicated by ) of the screen, and is laid on reference point P.

After the set point is settled in this manner, the position of reference point P on the image is given by (X0, Y0), which is regarded as a target value (set point on the monitor screen). The position (X, Y) of reference point P in each frame, in the screen shot continuously, is obtained, and the difference between this current position (X, Y) and the target value (X0, Y0) is calculated. Thus, a deviation ($\Delta X$, $\Delta Y$) as a movement on the monitor screen is obtained. The manipulated variable of jet-direction control means 104 is adjusted in response to a signal indicative of the deviation.

Thus, jet-direction control means 104 causes jet-direction changing fin 96 to rock so that the movement of the raised distal end portion of insertion section 3 is zero, thereby redirecting the air jet from jet port 35.

The position of raised insertion section 3 is restored in an instant by the thrust of the jet. In this manner, deflective displacements detected one after another, and feedback control is effected such that the displacement becomes zero. Thus, the raised position of insertion section 3 can be stabilized, so that a stable image can be observed.

Alternatively, the feedback control may be effected by detecting the difference between the current position and the position for the directly preceding frame. In the second embodiment, moreover, the TV camera is mounted on an eyepiece portion of the borescope. Also in a so-called electronic borescope using a solid-state image sensing device, such as a CCD, however, the feedback control can be effected using a video signal in the same manner as in the second embodiment.

FIGS. 17 and 18 show a first modification of the second embodiment. In this modification, the operating means for changing the position of the raised distal end portion of insertion section 3 is modified. More specifically, a plurality of jet ports 35a and 35b for jetting a fluid are formed in jet port structure 7 which is attached to that part of insertion section 3 between flexible tube portion 4 and bending tube portion 5. The movement of insertion section 3 can be adjusted by controlling the relative rates of flow from ports 35a and 35b.

In this modification, right- and left-hand jet ports 35a and 35b are arranged evenly, and are connected to separate air tubes 37a and 37b, respectively. Each of tubes 37a and 37b is provided with three-port electropneumatic regulator 120, as shown in FIG. 17. Regulator 120, which is connected to compressed fluid source 25 through a regulator, filter, etc., can control the distribution ratio of the rates of flow from fluid source 25 to air tubes 37a and 37b. The electropneumatic regulator is operated by means of control unit 124 which is feedback-controlled by feedback circuit 122, which resembles the aforementioned feedback control means.

If raised insertion section 3 deflects to the right, the fluid is supplied more to and ejected more strongly from left-hand jet port 35a. If the raised insertion section deflects to the left, on the other hand, the fluid is supplied more to and ejected more strongly from right-hand jet port 36b. Thus, the position of the raised insertion section can be restored and stabilized.

Figure 19:
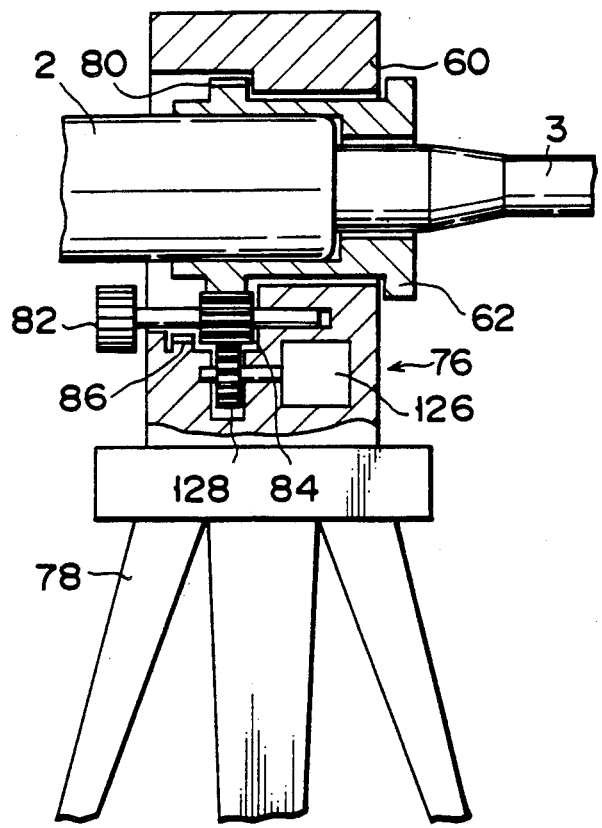
FIG. 19 is a partial sectional view showing a second modification of the borescope apparatus of FIG. 11.
Figure 22:
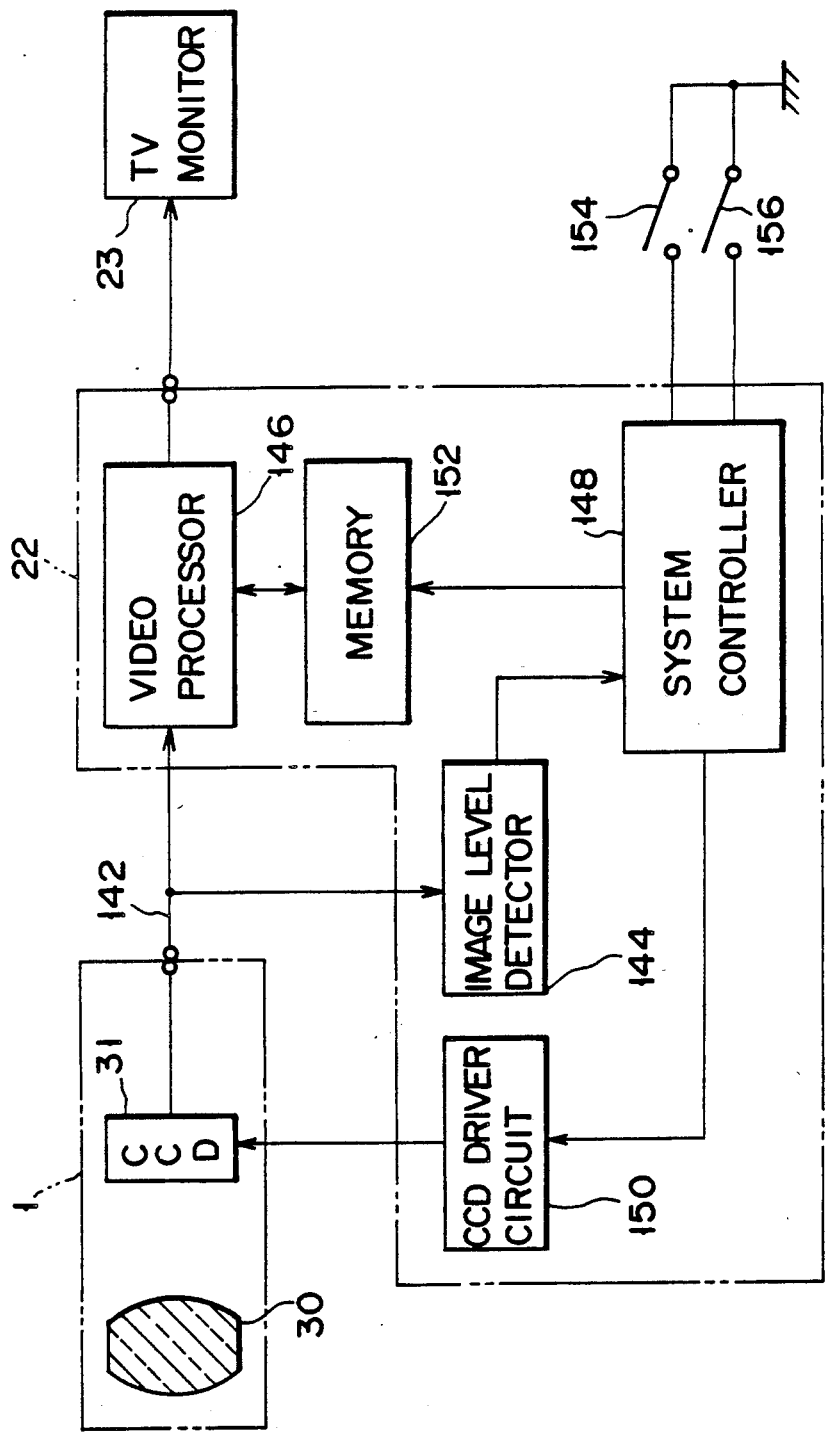
FIG. 22 is a block diagram showing a control circuit of the borescope apparatus of FIG. 20.
Figure 27:
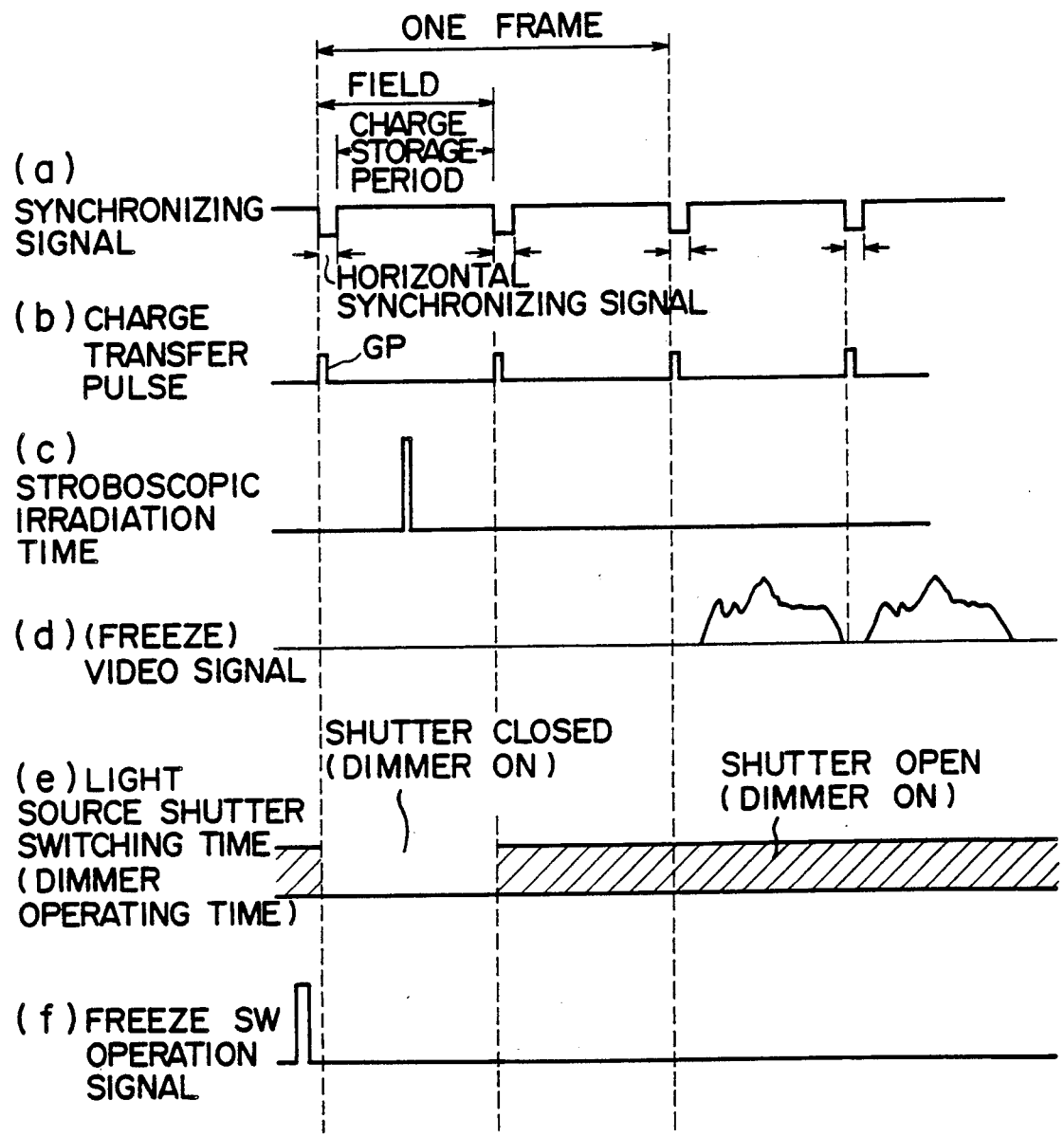
FIG. 27 is a timing chart for the control circuit shown in FIG. 26.

FIG. 19 shows a second modification of the second embodiment. In this modification, supporting device 76 for retaining operating section 2 of the borescope is used as operating means for finely adjusting the position of raised insertion section 3. In supporting device 76, fixed jig 60 is mounted on the top face of tripod 78, and movable jig 62 for engagedly supporting operating section 2 is rockably fitted in jig 60. Movable jig 62 has gear portion 80 thereon, and fixed jig 60 is provided with adjusting gear 84, corresponding to gear portion 80. Gear 84 is in mesh with gear portion 80 of movable jig 62, as shown in FIG. 19. Adjusting gear 84 is movable in the axial direction thereof, and can be detachably anchored to fixed tooth portion 86 on fixed jig 60. Gear 84, which normally is disengaged from tooth portion 86, as shown in FIG. 19, can be anchored to portion 86 by pulling and axially moving knob 82 of gear 84. Fixed jig 60 is further provided with operating motor 126, and small gear 128 is mounted on the rotating shaft of motor 126. Gear 128 is coupled to gear portion 80 of movable jig 62 by means of adjusting gear 84 as an intermediate gear.

In raising and twisting insertion section 3 of the borescope supported by supporting device 76, operating motor 126 is driven to rotate movable jig 62 through the medium of small gear 128 and adjusting gear 84. Thereupon, the borescope, which is integral with movable jig 62, rotates. The direction and amount of this rotation can be freely selected. By this operation, insertion section 3 can be twisted. Thus, if insertion section 3 of the jet-operated borescope supported by supporting device 76 is twisted as it is raised, its jet port is redirected, and the rising direction is changed. This arrangement constitutes the operating means for changing the position of the raised distal end portion of insertion section 3.

As mentioned before, therefore, raised insertion section 3 can be operated without deflection, that is, the raised position of section 3 can be stabilized, by controlling operating motor 126 by means of deflection detecting means for detecting the deflective displacement of the raised distal end portion of insertion section 3, and control means which effects feedback control in response to a signal from the detecting means so that the displacement of the raised distal end portion of section 3 is zero. Thus, a stable image can be observed.

According to supporting device 76 of this modification, insertion section 3 of the borescope can be also manually twisted. More specifically, it can be twisted by only turning knob 82 of adjusting gear 84. Further, insertion section 3 can be fixed to a predetermined rotational position by pulling and axially moving knob 82 to anchor gear 84 to fixed tooth portion 86. By doing this, movable jig 62 is secured to fixed jig 60.

The following is a description of a third embodiment of the present invention. In borescope 1 according to this third embodiment, as shown in FIG. 20, insertion section 3 is connected to operating section 2. Section 3 includes flexible tube portion 4 extending from operating section 2, bending tube portion 5, and distal end portion 6, connected in succession. As in a conventional endoscope, windows for observation and illumination are arranged at distal end portion 6 of insertion section 3.

Jet port 35 for jetting a fluid, such as air, is formed at the bottom portion of jet port structure 7, which connects flexible tube portion 4 and bending tube portion 5. Port 35 is connected with one end of an air tube which is passed through insertion section 3, operating section 2, and universal cord 130 extending from section 2. The other end of the air tube is connected to a compressed fluid source which is incorporated in external electric light source unit 132. Operating section 2 of borescope 1 is provided with flow control switch 134, and the flow rate of the fluid supplied from the compressed fluid source to jet port 35 can be controlled by operating switch 134. Section 2 is further provided with bending control knob 15 for bending the bending tube portion.

Connector 136, which is attached to the extended end of universal cord 130, is removably connected to electric light source unit 21. Unit 21 contains a light source for illumination, a power source, etc., as well as the compressed fluid source. Power switch 138, illumination light adjusting knob 140, etc. are arranged on the front face of the housing of light source unit 21.

Signal cable 142, which diverges from connector 136 of universal cord 130, is connected with camera control unit 22. Unit 22 is connected to solid-state image sensing device or charge-coupled device (CCD) 31 at digital end portion 6 of insertion section 3 by means of signal cord 142 and universal cord 130. CCD 31 used may be of the interline-type, for example.

An image of the subject is formed on a photosensitive screen of CCD 31 by means of objective lens 30. A photoelectric conversion signal delivered from a signal output terminal of CCD 31 after photoelectric conversion is transmitted through signal cable 142 to camera control unit 22, and is supplied to image level detector 144 and video processor 146. Processor 146 fetches the output signal of CCD 31 applied thereto, converts it into a standardized video signal of e.g. the NTSC system, and delivers the video signal to TV monitor 23.

Image level detector 144 detects the level of the output signal of CCD 31, and converts it into a DC signal. Detector 144 delivers a DC voltage of a level proportional to the output level of CCD 31.

Further, camera control unit 22 is provided with system controller 148, and the operation of CCD 31 is controlled by means of CCD driver circuit 150, thereby effecting a shutter function. In response to the level of the output signal of CCD 31 detected by image level detector 144, electric charges stored in photodiodes which constitute CCD 31 are read out at high speed, whereby the storage of the charges is prohibited for a fixed period of time. Thus, shutter means is arranged which restricts the actual charge storage time for image sensing operation within the range of charge storage time. More specifically, the electric charges stored in the photodiodes are swept away by being quickly read out, and subsequently stored charges are used for actual image display. Thus, the actual image-sensing charge storage time is restricted to a duration shorter than the original image-sensing charge storage time, so that the shutter function can be fulfilled.

The actual image-sensing charge storage time is changed in accordance with the level of the output signal of CCD 31 detected by image level detector 144. Thus, the storage time is shortened when the output level of CCD 31 is high. When the output level of CCD 31 is low, on the other hand, the storage time is lengthened. The extent of this adjustment may be changed depending on the working conditions and purposes. In general, however, it is to be desired that the storage time should be minimized to ensure a satisfactory shutter function provided it is long enough for good exposure (light sensing).

The output signal of CCD 31 can be digitized in video processor 146, and the resulting digital signal can be stored in image memory 152. For example, a field memory may be used as image memory 152.

The digital signal is stored in image memory in response to an operation signal from freeze switch 154, and is then read out and converted into a standardized video signal of e.g. the NTSC system. The video signal is delivered to TV monitor 23, thereupon a still picture is displayed. This still picture is obtained by, so to speak, instantaneous photographing, with the actual image-sensing charge storage time restricted to a duration shorter than the original image-sensing charge storage time of CCD 31. Therefore, a distinct picture can be obtained despite a fairly sharp deflection of raised insertion section 3. Freeze switch 154 may be provided on operating section 2 of borescope 1 or the front face of the housing of electric light source unit 21, or on each of the two.

In response to an operation signal from mode switch 156 on the front face of the housing of electric light source unit 21, for example, the operation mode can be switched between a special mode, in which an image is sensed by using the shutter function during the observation of animated pictures, and a normal mode in which the shutter function is off. When mode switch 156 is operated, system controller 148, receiving the operation signal from the switch, adjusts CCD driver circuit 150 to control the operation of CCD 31, thereby effecting the shutter function.

When using the borescope apparatus constructed in this manner, insertion section 3 of borescope 1 is introduced into the object of inspection through inspection hole 160, which is bored through wall portion 158 of the object. Then, the insertion section is raised by jetting the compressed air from jet port 35. In the normal or special mode, distal end portion 6 of insertion section 3 is guided to inspection region A, as shown in FIG. 20, while observing the internal state of the object of inspection in the form of a real-time monitor picture displayed on TV monitor 23, as shown in FIG. 21.

If a still picture is required for close a inspection, freeze switch 154 is operated. In response to an operation signal from switch 154, system controller 148 controls the operation of CCD driver circuit 150, thereby effecting the shutter function for the image sensing operation. Also, the output signal of CCD 31 is digitized and stored in image memory 152 of video processor 146. Processor 146 reads out the digital signal, converts it into a standardized video signal of e.g the NTSC system, and delivers the video signal to TV monitor 23. Thus, a still picture is displayed on the monitor.

An operator can observe the still picture thus obtained, thereby making a close examination. As mentioned before, the still picture is obtained by the instantaneous photographing, with the actual image-sensing charge storage time restricted to a duration shorter than the original image-sensing charge storage time of CCD 31. Therefore, a distinct still picture can be obtained despite a fairly sharp deflection of raised insertion section 3. Alternatively, the still picture may be recorded or photographed.

In the jet-operated borescope apparatus constructed in this manner, even normal observation is essentially not easy due to tossing of insertion section 3. Therefore, it is advisable rather to obtain a blur-free still picture for a close inspection. If the aforementioned shutter function is used, the still picture obtained by freezing is much more distinct than a blurred ordinary still picture. Thus, the shutter function is suited for the borescope of this type.

FIG. 23 shows a modification of the shutter means. In this modification, the actual image-sensing charge storage time is restricted within the range of the image-sensing charge storage time of CCD 31 by means of liquid-crystal shutter 169, depending on the level of the output signal of CCD 31 detected by image level detector 144. More specifically, liquid-crystal shutter 169 for use as the shutter means is provided in front of the photosensitive screen of CCD 31. In performing freezing operation, shutter 169 is opened in synchronism with the image sensing operation of CCD 31. Thus, instantaneous photographing can be effected with the actual image-sensing charge storage time restricted to a duration shorter than the original image-sensing charge storage time of CCD 31.

FIGS. 24 to 27 show a fourth embodiment of the present invention. Operating section 2 of borescope 1 according to this fourth embodiment is provided with eyepiece portion 162. Image guide 44 is passed through operating section 2 and insertion section 3 of borescope 1. The leading end of image guide 44 faces objective lens 30 at distal end portion 6 of section 3, while the trailing end of guide 44 is connected to eyepiece lens system 164 of eyepiece portion 162. Light guide 33 is passed through operating section 2, insertion section 3, and universal cord 130 of borescope 1. The leading end of light guide 33 faces illumination window 34 at distal end portion 6 of insertion section 3, while the trailing end of guide 33 is guided to connector 136 at the extended end of cord 130. As connector 136 is removably connected to electric light source unit 21, an illumination light is transmitted from illumination light source 166 in unit 21 to light guide 33.

Inside electric light source unit 21, shutter 168 is located on optical path 1 of illumination light source 166. Shutter 168 is controlled by means of shutter driver circuit 170, as shown in FIG. 26.

As shown in FIG. 24, power switch 138, illumination light adjusting knob 140, etc. are arranged on the front face of the housing of electric light source unit 21.

TV camera 172 is attached to eyepiece portion 28 of borescope 1. As shown in FIG. 26, camera 172 is provided with image sensing lens 174 and solid-state image sensing device or charge-coupled device (CCD) 31. An image observed through eyepiece portion 28 is focused as a subject on the photosensitive screen of CCD 31. An image signal obtained by photoelectric conversion by means of CCD 31 of TV camera 172 is transmitted through signal cord 142 to camera control unit 22. CCD 31 used may be of the interline-type, for example.

The output signal of CCD 31 is applied to video processor 146 of camera control unit 22. Processor 146 fetches the output signal of CCD 31, converts it into a standardized video signal of e.g. the NTSC system, and delivers the video signal to TV monitor 23.

Camera control unit 22 is provided with system controller 148, which controls the image sensing operation CCD 31 through the medium of CCD driver circuit 150. Also, the output signal of CCD 31 may be stored in image memory 152 attached to video processor 146. For example, a field memory may be used as image memory 152.

In response to an operation signal from freeze switch 154, the video signal is stored in image memory 152, read out and converted into a standardized video signal of e.g. the NTSC system, and then delivered to TV monitor 23. Thus, a still picture is obtained.

Freeze switch 154 is provided at operating section 2 of borescope 1. Alternatively, it may be located on the front face of the housing of electric light source unit 21 or on each of the two regions.

As shown in FIG. 26, moreover, stroboscopic luminous body 176 is provided distal end portion 6 of insertion section 3. Luminous body 176 is positioned so that light therefrom is directed to field A of view of borescope 1. Stroboscopic luminous body 176 is driven to glow by stroboscopic glow driver circuit 178 in cam era control unit 22.

When using the borescope apparatus constructed in this manner, insertion section 3 of borescope 1 is introduced into the object of inspection through inspection hole 160, which is bored through wall portion 158 of the object. In general, CCD 31 is driven in normal image sensing operation. The output signal of CCD 31 is applied to video processor 146 of camera control unit 22. Processor 146 fetches the output signal of CCD 31, converts it into a standardized video signal of e.g. the NTSC system, and causes TV monitor 23 to display a real-time image of the interior of the object of inspection, as shown in FIG. 25.

While the real-time monitor picture is being observed, distal end portion 6 of insertion section 3 is guided to inspection region B, as shown in FIG. 24.

If a still picture is required for a close inspection, freeze switch 154 is operated. In response to an operation signal from switch 154, system controller 148 controls the respective operations of shutter driver circuit 170, CCD driver circuit 150, and stroboscopic glow driver circuit 178, thereby effecting the following freezing operation.

When the operation signal from freeze switch 154 is inputted, as shown in FIG. 27(f), CCD 31 quickly sweeps away electric charges stored in the preceding field, in accordance with transfer pulse GP in a first-stage (odd-number-stage) field shown in FIG. 27(b), in time with a synchronizing signal shown in FIG. 27(a). At the same time, shutter 168 of illumination light source unit 21 is closed, as shown in FIG. 27(e), and is kept closed during the first-stage field. Accordingly, observation field A of borescope 1 is dark, and the illumination light cannot be incident on the photosensitive screen of CCD 31 through light guide 33. Thus, CCD 31 cannot be stored with new charges by the illumination light.

After the electric charges stored in the preceding field are swept away, in these circumstances, stroboscopic luminous body 176 glows, as shown in FIG. 27(c), thereby instantaneously illuminating the dark field of observation. This illumination allows a field image to be focused as a subject image on the photosensitive screen of CCD 31 through image guide 44, eyepiece lens system 164 at eyepiece portion 28, and image sensing lens 174 of TV camera 172. Photodiodes of CCD 31 photoelectrically convert this image, thereby accumulating electric charges in a short period of time. Thus, the image is instantaneously sensed in a very short time (e.g., 1/10,000 seconds or less) which is shorter than the original image-sensing charge storage time of CCD 31, so that an apparently still image can be obtained even while insertion section 3 is tossing sharply. In consequence, a very distinct picture can be enjoyed.

The electric charges thus stored in CCD 31 are normally read out and transferred in the next field, in response to a charge transfer pulse GP for the next field, and are delivered to video processor 146. At this point of time, shutter 168 of illumination light source unit 21 may be open, and thereafter, it is kept open, as shown in FIG. 27(e).

In video processor 146, the output signal from CCD 31 is digitized and stored in image memory 152. The stored signal is read out at the time for the next frame, converted into a standardized video signal of e.g. the NTSC system, and delivered to TV monitor 23. Thus, a still picture is displayed on the monitor, as shown in FIG. 27(d).

The operator can observe the still picture thus obtained, thereby making a close examination. As mentioned before, the still picture is obtained by the instantaneous photographing, with the actual image-sensing charge storage time restricted by the stroboscopic glow to a duration shorter than the original image-sensing charge storage time of CCD 31. Therefore, a very distinct still picture can be obtained despite a fairly sharp deflection of raised insertion section 3. Alternatively, the still picture may be recorded or photographed.

In the jet-operated borescope apparatus constructed in this manner, even normal observation is essentially not easy due to tossing of insertion section 3. Therefore, it is advisable rather to obtain a blur-free still picture for a close inspection. The still picture obtained by freezing using the stroboscopic glow is much more distinct than a blurred ordinary still picture.

Shutter 168 of illumination light source unit 21 is not limited to the arrangement in which it can be fully closed, and may be of a dimmer type which is adapted to reduce the intensity of illumination light applied to the field of observation. This dimmer shutter can provide the same function and effect of the fully-closable shutter.

In consideration of the same circumstances, shutter sometime need not be used. If the intensity of the stroboscopic glow is sufficiently higher than the brightness of field A of view, for example, the function of shutter 168 is unnecessary, due to automatic adjustment of the sensitivity of the CCD and its latitude.

The stroboscopic glow means may be any other system than the one in which stroboscopic luminous body 176 is built in insertion section 3. For example, the luminous intensity of illumination light source unit 166 may be instantaneously increased, or a separate stroboscopic light source may be turned on.

Alternatively, moreover, the borescope may be a so-called electronic borescope in which image sensing CCD 31 is built in distal end portion 6 of insertion section 3.

Figure 28:
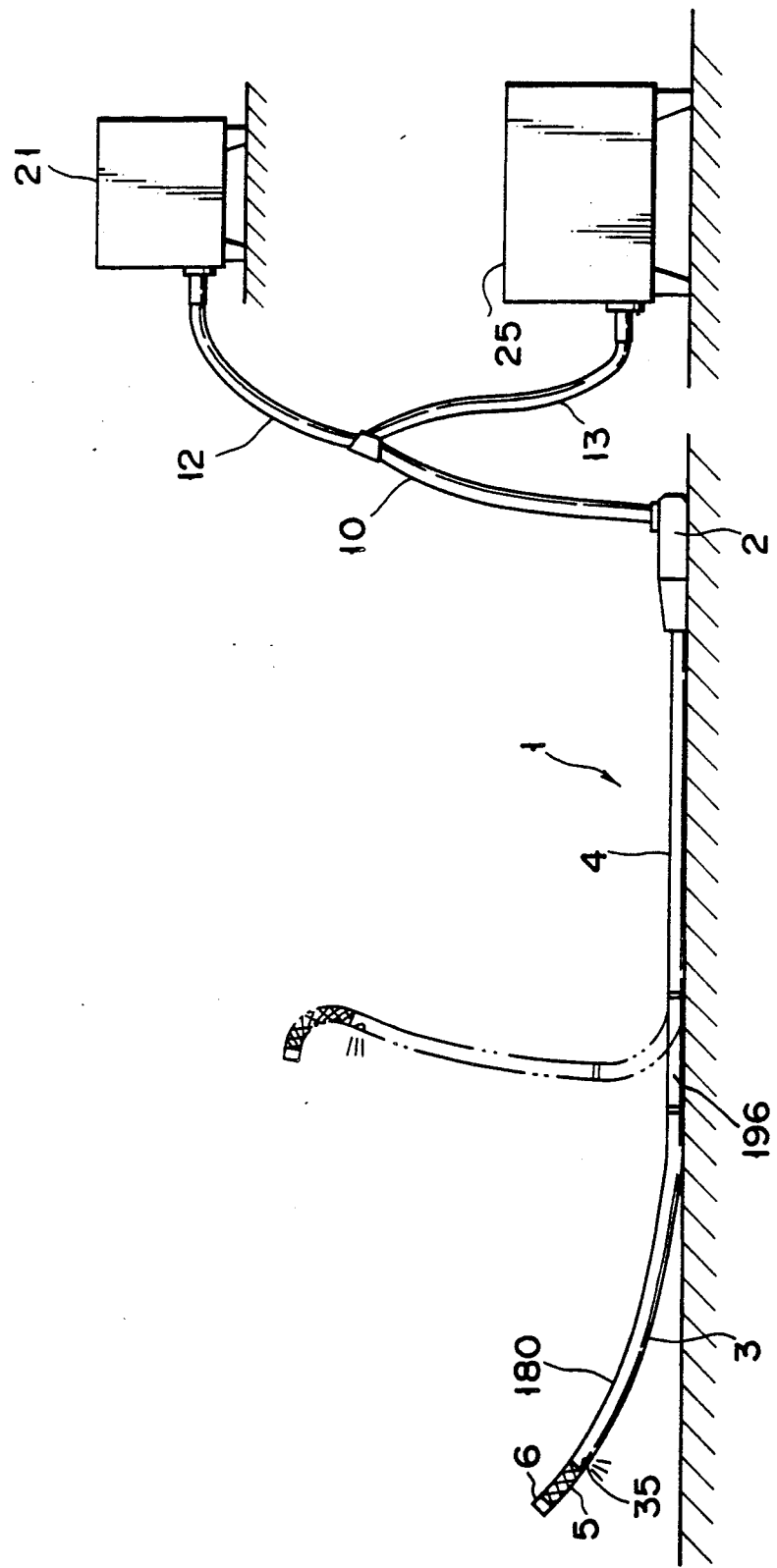
FIG. 28 is a side view showing an operating state of a borescope apparatus according to a fifth embodiment of the present invention.
Figure 29:
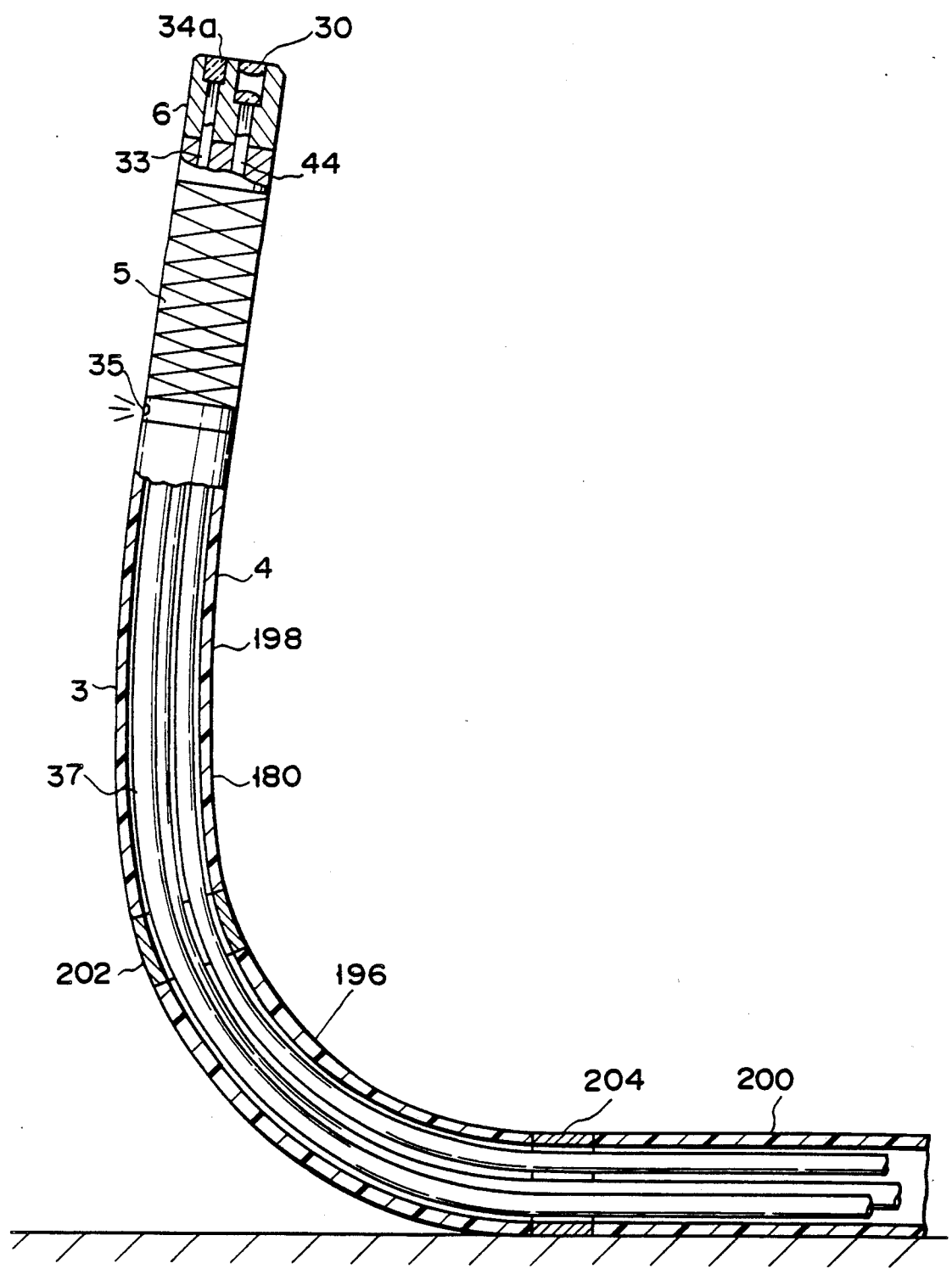
FIG. 29 is a partial sectional view of an insertion section of the borescope apparatus shown in FIG. 28.

Referring now to FIGS. 28 and 29, a fifth embodiment of the present invention will be described. FIG. 29 shows an arrangement of the principal part of a jet-operated borescope apparatus shown in FIG. 28

In FIG. 28, numeral 1 denotes a jet-operated borescope. Borescope 1 comprises operating section 2, insertion section 3, and bifurcate universal cord 10. Operating section 2 is connected with the proximal end portion of insertion section 3 and one end portion of cord 10. Connecting ends of branch cords 12 and 13 are detachably connected to light source unit 21 and compressor unit 25, respectively.

Insertion section 3 is formed of flexible tube portion 4, bending tube portion 5, and distal end portion 6. The proximal end of flexible tube portion 4 is connected to operating section 2, and distal end portion 6 is connected to the distal end of tube portion 4 by means of bending tube portion 5.

Arranged in insertion section 3, as shown in FIG. 29, are image guide fiber 44, for use as image transfer means, light guide fiber 33, for use as illumination light transfer means, and fluid tube 37 for feeding a fluid from compressor unit 25. In this case, the distal ends of fibers 44 and 33 are optically connected to objective lens 30 and illumination lens 34a, respectively, in distal end portion 6 of insertion section 3.

Fluid jet port 35 is formed between flexible tube portion 4 and bending tube portion 5 of insertion section 3. The distal end portion of air tube 37 is connected to port 35. Tube 37 extends through operating section 2 and branch cord 13 of universal cord 10, and its proximal end is detachably connected to compressor unit 25.

When the high-pressure fluid is supplied from unit 25 to fluid jet port 35 through air tube 37, it is jetted in the radial direction of insertion section 3 from port 35. Thus, the distal end portion of insertion section 3 can be raised by a thrust produced by the high-pressure fluid jet from port 35.

Preventive means is provided for preventing distal rising portion 180 of insertion section 3 from toppling down toward operating section 2. In this preventive means, relatively short intermediate tube member 196 with high flexibility (or low rigidity) is disposed in the middle of flexible tube portion 4, and front and rear tube members 198 and 200 with low flexibility (or high rigidity) are arranged in front and in the rear, respectively, of member 196. In this case, intermediate tube member 196 is situated near the lower end of rising portion 180 of insertion section 3. If flexible tube portion 4 has a diameter of 11 mm, for example, the length of member 196 preferably ranges from about 5 to 10 cm. It is understood that the length of member 196 may be changed in accordance with the flexibility of the flexible tube portion. The front end portion of intermediate tube member 196 and front tube member 198 are connected by means of first connector ring 202, while the rear end portion of member 196 and rear tube member 200 are connected by means of second connector ring 204. Intermediate tube member 196 has a suitable length and flexibility such that distal rising portion 180 of insertion section 3 can be prevented from toppling down toward operating section 2 even when the flow rate of the high-pressure fluid jetted from fluid jet port 35 is maximized, and that rising portion 180 of insertion section 3 can be raised to the highest point.

The following is a description of the operation of the borescope apparatus constructed in this manner.

First, insertion section 3 of borescope 1 is inserted into a bore of an object of inspection, and its distal end portion 6 is guided to a suitable position. In this state, the high-pressure fluid is supplied from compressor unit 25 to fluid jet port 35 through air tube 37, and is jetted in the radial direction of insertion section 3 from port 35. Thus, the distal end portion of insertion section 3 can be raised by a thrust produced by the high-pressure fluid jet from port 35.

At this time, the distal rising portion 180 of insertion section 3 is raised, while intermediate tube member 196 with high flexibility curves mainly. In this case, if the flow rate of the fluid from port 35 is increased, the height of rising portion 180 of insertion section 3 increases, so that the radius of curvature of intermediate tube member 196 is reduced depending on the height of rising portion 180, thereby the tube member 196 becoming hard to bend gradually. The reaction force of tube member 196 acting on insertion section 3 increases in proportion as the height of rising portion 180 increases, so that the rising movement of rising portion 180 can be stopped at the predetermined position.

Thus, even though the flow rate of the high-pressure fluid jet from port 35 is constant, as in the case of the conventional arrangement, distal rising portion 180 of insertion section 3 can be prevented from toppling down toward operating section 2. In FIG. 28, a broken line indicates the position where rising portion 180 is at a standstill.

Thus, in the borescope with the aforementioned construction, when the high-pressure fluid is ejected from fluid jet port 35 at the distal end portion of insertion section 3 to the distal end portion of section 3, distal rising portion 180 of section 3 can be prevented from toppling down by means of intermediate tube member 196 near the lower end of rising portion 180. Accordingly, stable observation can be effected with the distal end of insertion section 3 raised. In contrast with the conventional case, moreover, the distal end of insertion section 3 can be prevented from being damaged by running against a wall or the like.

Figure 30:
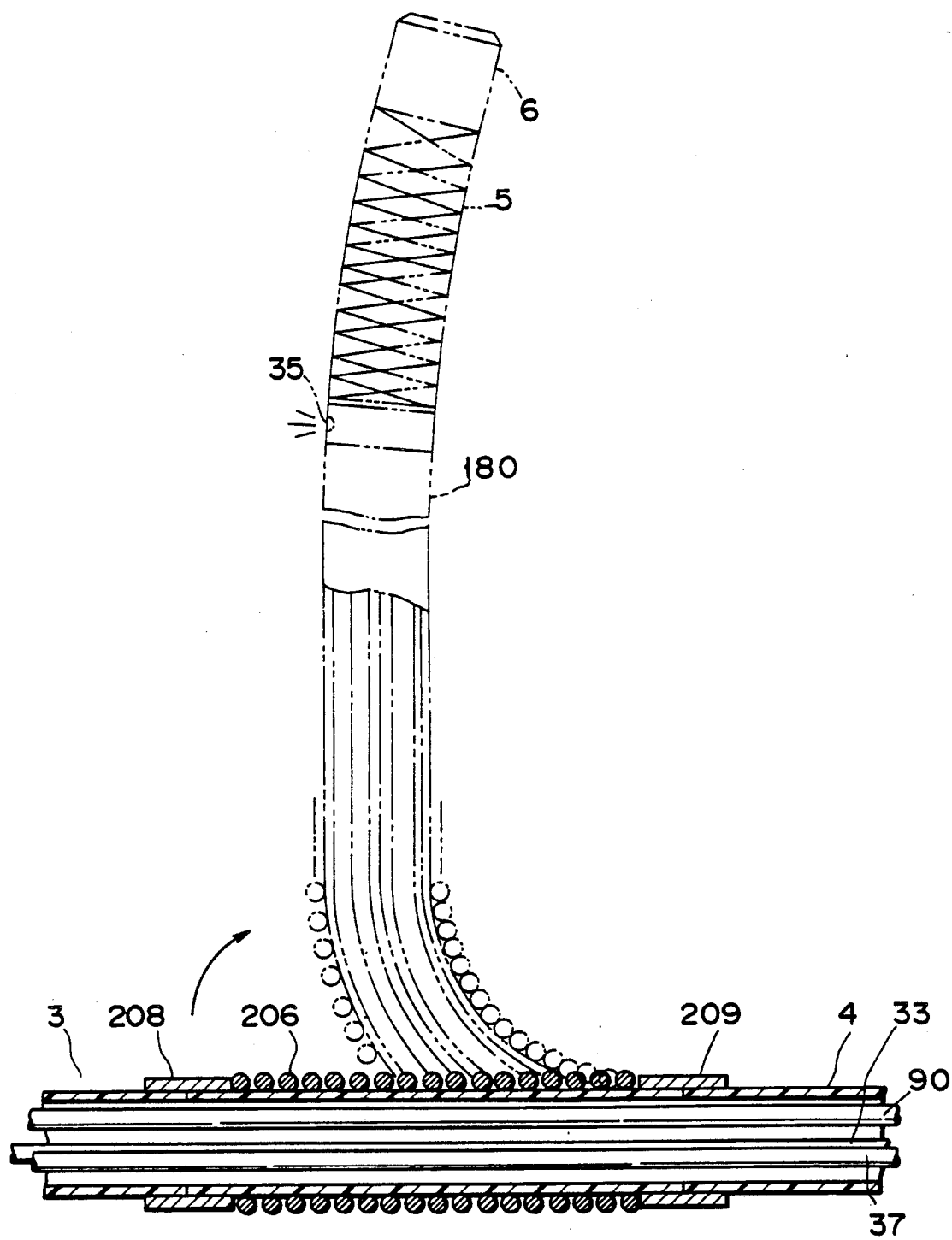
FIG. 30 is a partial sectional view showing a first modification of the borescope apparatus of FIG. 28.

FIG. 30 shows a first modification of the fifth embodiment. In this modification, coil spring 206 is disposed on the outer peripheral surface of flexible tube portion 4, to serve as the preventive means for preventing distal rising portion 180 of insertion section 3 from toppling down toward operating section 2. In this case, spring 206 is located near the lower end of rising portion 180 of section 3, and its two opposite ends are retained individually by means of connector rings 208 and 209. Spring 206 is just resilient enough to prevent distal rising portion 180 of insertion section 3 from toppling down toward operating section 2 even when the flow rate of the high-pressure fluid jetted from fluid jet port 35 is maximized.

In this first modification, when the high-pressure fluid is jetted from fluid jet port 35 at the distal end portion of insertion section 3 so that the distal end portion of section 3 is raised by the thrust produced by the fluid jet, coil spring 206 on the outer peripheral surface of flexible tube portion 4 bends substantially in the form of a circular arc, as indicated by broken lines in FIG. 30. In this case, if the flow rate of the fluid from port 35 is increased, the height of rising portion 180 of insertion section 3 increases. As the position of rising portion 180 rises, therefore, the radius of curvature of the substantially arcuately bent portion of coil spring 206 is reduced, so that the restoring force of the spring gradually increases. Even when the flow rate of the high-pressure fluid jetted from fluid jet port 35 is maximized, therefore, the restoring force of spring 206 can prevent distal rising portion 180 from toppling down toward operating section 2.

Figure 31:
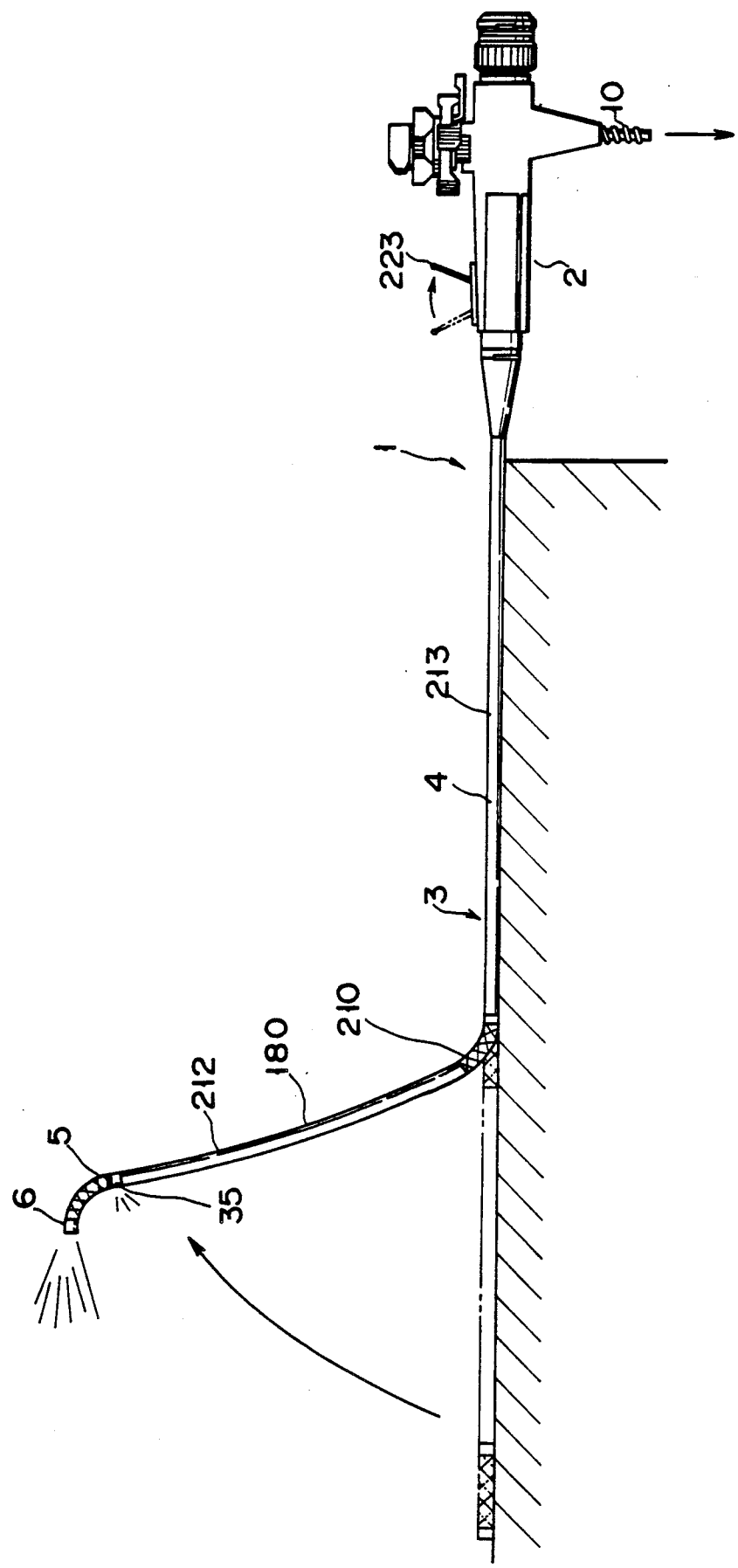
FIG. 31 is a side view showing an operating state of a borescope apparatus according to a second modification of the fifth embodiment.

FIGS. 31 to 33 show a second modification of the fifth embodiment. In this modification, as shown in FIG. 31, height adjusting portion 210 is disposed in the middle of flexible tube portion 4, to serve as the preventive means for preventing distal rising portion 180 of insertion section 3 from toppling down toward operating section 2, and rear tube members 212 and 213 with low flexibility are arranged in front and in the rear, respectively, of adjusting portion 210. In this case, height adjusting portion 210 is located near the lower end of rising portion 180 of insertion section 3.

Height adjusting portion 210 includes flexible sheathing tube 214 and a plurality of bending segments 216 therein. Each end portion of each segment 216 is connected to its facing end of each adjacent segment 216 so as to be rockable around connecting pin 215. In this case, front-end bending segment 216a and front tube member 212 are connected by means of first connector ring 217, while rear-end bending segment 216b and rear tube member 213 are connected by means of second connector ring 218.

As shown in FIG. 33, insertion section 3 contains four angle wires 219 for the bending control of bending tube portion 5 and protector tubes 220 for protecting the wires, as well as image guide fiber 44, light guide fiber 33, and fluid tube 37. The insertion section further contains one angle wire 221 for adjusting the height of insertion section 3 and protector tube 222 for protecting wire 221. In this example, wire 221 and tube 222 are located in the same direction as fluid jet port 35, with respect to the circumferential direction of insertion section 3. The respective distal end portions of four angle wires 219 for the bending control are fixed to bending segments (not shown) of bending portion 5. The respective proximal end portions of wires 219 are connected to angle knobs in operating section 2. The distal end portion of angle wire 221 for adjusting the height of insertion section 3 is fixed to the inner surface of front-end bending segment 216a of height adjusting portion 210 so as to extend in the same direction as jet port 35. The proximal end portion of wire 221 is connected to height adjusting lever 223 in operating section 2.

In this second modification, when the high-pressure fluid is jetted from fluid jet port 35 at the distal end portion of insertion section 3 so that the distal end portion of section 3 is raised by the thrust produced by the fluid jet, height adjusting lever 223 in operating section 2 is operated as indicated by an arrow in FIG. 31, so that front-end bending segment 216a of height adjusting portion 210 is pulled to the right of FIG. 32 by means of angle wire 221. By doing this, the thrust produced by the high-pressure fluid jet from fluid jet port 35 is balanced with a tension acting on wire 221. Thus, rising portion 180 at the distal end portion of insertion section 3 can be stopped at any desired raised position. In this case, the manipulated variable of height adjusting leer 223 can be adjusted to change the stroke of angle wire 221, thereby adjusting the height of rising portion 180 at the distal end portion of insertion section 3.

When height adjusting lever 223 is moved to its action-limit position, top-side slant end portions of bending segments 216 of height adjusting portion 210 are brought into contact with one another. In this state, therefore, adjusting portion 210 is bent to the utmost limit, and cannot be further bent. Thus, distal rising portion 221 of insertion section 3 can be prevented from toppling down, so that stable observation can be effected with the distal end of section 3 kept raised.

The present invention is not limited to the embodiments described above. In the aforementioned embodiments, for example, fluid jet port 35 is located between flexible tube portion 4 and bending tube portion 5 of insertion section 3. Alternatively, however, port 35 may be located between bending tube portion 5 and distal end portion 6.

Further, angle wire 221 and protector tube 222 of the modification shown in FIGS. 31 to 33 may be situated diametrically opposite to fluid jet port 35, with respect to the circumferential direction of insertion section 3. In this case, height adjusting portion 210 can be bent in the same direction as the thrust produced by the high-pressure fluid jet from port 35, thereby facilitating the rising action of distal rising portion 180 of insertion section 3.

It is to be understood, moreover, that various changes and modifications may be effected in the present invention by one skilled in the art without departing from the scope or spirit of the invention.

What is claimed is:

1. A borescope apparatus comprising:
   a flexible insertion section having an axis;
   a jet port formed at the insertion section for ejecting a fluid;
   moving means for supplying a compressed fluid to the jet port, whereby the insertion section is moved by an impellent force of the fluid ejected from the jet port; and
   stabilizing means for steadily maintaining a position of the insertion section;
   said stabilizing means including jet-angle control means disposed adjacent to the jet port for varying the jet angle of the compressed fluid with respect to the axis of the insertion section; and
   said jet-angle control means including a valve member for changing the jet angle of the fluid, and urging means for urging the valve member in a direction such that the jet angle increases, said valve member being adapted to reduce the jet angle, resisting the urging force of the urging means, when subjected to a pressure from the compressed fluid.

2. The borescope apparatus according to claim 1, wherein said jet-angle control means includes an actuator for adjusting the position of the valve member.

3. The borescope apparatus according to claim 1, wherein said insertion section is arranged so that at least the distal end portion thereof is rotatable around the axis thereof, and said stabilizing means includes rotating means for rotating at least the distal end portion of the insertion section.

4. The borescope apparatus according to claim 1, wherein said stabilizing means includes deflection detection means for detecting a deflective displacement at the distal end portion of the insertion section, and movement control means for controlling the moving means in accordance with a signal from the deflection detecting means so that the deflective displacement at the distal end portion is zero.

5. The borescope apparatus according to claim 1, wherein said moving means comprises raising means for raising the distal end portion of the insertion section, and said stabilizing means comprises posture maintaining means for steadily maintaining a raised posture of the insertion section.

6. A borescope apparatus comprising:
   a flexible insertion section;
   a jet port formed at the insertion section for ejecting a fluid;
   moving means for supplying a compressed fluid to the jet port, whereby the insertion section is moved by an impellent force of the fluid ejected from the jet port; and
   stabilizing means for steadily maintaining a position of the insertion section;
   said stabilizing means including deflection detecting means for detecting a deflective displacement at the distal end portion of the insertion section, and movement control means for controlling the moving means in accordance with a signal from the deflection detecting means so that the deflective displacement at the distal end portion is zero.

7. The borescope apparatus according to claim 6, which further comprises image sensing means including an objective optical system arranged at the distal end portion of the insertion section, and wherein said deflection detecting means includes means for detecting a displacement at a reference point on an image obtained from the image sensing means.

8. The borescope apparatus according to claim 6, wherein said moving means includes jet-angle control means for varying the jet angle of the compressed fluid with respect to the axis of the insertion section.

9. The borescope apparatus according to claim 6, wherein said moving means includes jet-direction changing means for changing the jet direction of the compressed fluid in the circumferential direction of the insertion section.

10. The borescope apparatus according to claim 9, wherein said jet-direction changing means comprises a flap rockably disposed in front of the jet port.

11. The borescope apparatus according to claim 9, wherein said insertion section has a plurality of jet ports, and said jet-direction changing means includes means for changing the relative flow rate of the fluid supplied to the jet ports.

12. The borescope apparatus according to claim 9, wherein said insertion section is arranged so that at least the distal end portion thereof is rotatable around the axis thereof, and said jet-direction changing means includes rotating means for rotating at least the distal end portion of the insertion section.

13. The borescope apparatus according to claim 12, wherein said rotating means includes a tool for retaining and rotating the borescope apparatus around the axis of the insertion section.

14. A method of observation using a borescope apparatus, comprising steps of:
    raising a flexible insertion section of a borescope which includes an insertion section, a jet port formed at the insertion section for ejecting a fluid, and raising means for supplying a compressed fluid to the jet port, whereby the insertion section is raised by an impellent force of the fluid ejected from the jet port;
    observing a moving image converted form a video signal from an image sensing system attached to the borescope; and
    limiting a charge storage time of the image sensing system to a value within a given range, and converting a sensed video signal into a frozen image and observing the frozen image, when the raised insertion section of the borescope undesirably deflects.

* * * * *